US012018299B2

(12) United States Patent
Ronning

(10) Patent No.: US 12,018,299 B2
(45) Date of Patent: Jun. 25, 2024

(54) METHODS AND KITS FOR QUANTIFYING ADENOSINE-CONTAINING MOLECULES

(71) Applicant: SEVIVO LLC, Omaha, NE (US)

(72) Inventor: Donald R. Ronning, Omaha, NE (US)

(73) Assignee: SEVIVO LLC, Omaha, NE (US)

( * ) Notice: Subject to any disclaimer, the term of this patent is extended or adjusted under 35 U.S.C. 154(b) by 786 days.

(21) Appl. No.: 16/956,435

(22) PCT Filed: Dec. 20, 2018

(86) PCT No.: PCT/US2018/066817
§ 371 (c)(1),
(2) Date: Jun. 19, 2020

(87) PCT Pub. No.: WO2019/126512
PCT Pub. Date: Jun. 27, 2019

(65) Prior Publication Data
US 2020/0339970 A1    Oct. 29, 2020

Related U.S. Application Data

(60) Provisional application No. 62/608,011, filed on Dec. 20, 2017.

(51) Int. Cl.
C12N 9/24       (2006.01)
C12Q 1/34       (2006.01)
C12Q 1/48       (2006.01)

(52) U.S. Cl.
CPC ............ C12N 9/2497 (2013.01); C12Q 1/34 (2013.01); C12Q 1/48 (2013.01); C12Y 302/02016 (2013.01); C12N 2320/10 (2013.01); G01N 2333/91011 (2013.01)

(58) Field of Classification Search
CPC .... C12N 9/2497; C12N 2320/10; C12Q 1/34; C12Q 1/48; C12Y 302/02016; G01N 2333/91; G01N 2333/91011
See application file for complete search history.

(56) References Cited

FOREIGN PATENT DOCUMENTS

WO    WO-2009078876 A1 *  6/2009  ............. C07K 16/44

OTHER PUBLICATIONS

Blum et al. "Using Azido Analogue of S-Adenosyl-L-Methionine for Bioorthogonal Profiling of Protein Methylation (BPPM)", Current Protocols in Chemical Biology, Mar. 1, 2013, vol. 5, pp. 45-66. (Year: 2013).*
Graves et al. "A universal competitive fluorescence polarization activity assay for S-adenosylmethionine utilizing methyltransferases", Analytical Biochemistry, 2008, vol. 373, Issue 2, pp. 296-306. (Year: 2008).*
Hickey et al. "Structure-Guided Design of Fluorescent S-Adenosylmethionine Analogs for a High-Throughput Screen to Target SAM-I Riboswitch RNAs", Chemistry and Biology, Mar. 2014, vol. 21, Issue 3, pp. 345-356. (Year: 2014).*
Banco et al. "Neutron structures of Helicobacter pylori 5'-methylthioadenosine nucleosidase highlight proton sharing and protonation states", PNAS, Nov. 29, 2016, vol. 113, No. 48, pp. 13756-13761. (Year: 2016).*
Møller et al. "Selenium as an alternative peptide label—comparison to fluorophore-labelled penetratin", European Journal of Pharmaceutical Sciences, 2015, vol. 67: pp. 76-84. (Year: 2015).*
Nielsen et al. "Dual fluorescent labelling of cellulose nanocrystals for pH sensing", Chemical Communications, 2010, Issue 46, pp. 8929-8931. (Year: 2010).*
Sigma Website—Ro 41-0960 inhibitor information; https://www.sigmaaldrich.com/US/en/product/sigma/r108 (Year: 2023).*
Nanda et al. "Chapter 7—Labeling of a Protein with Fluorophores Using Maleimide Derivitization", Methods in Enzymology, 2014, vol. 536, pp. 79-86. (Year: 2014).*
Drake et al. "A Sensitive Luminescent Assay for the Histone Methyltransferase NSD1 and other SAM-Dependent Enzymes", Assay and Drug Development Technologies, Jun. 2014, vol. 12, No. 5, pp. 258-271. (Year: 2014).*
Mishra et al. "Crystal Structures of the Helicobacter pylori MTAN Enzyme Reveal Specific Interactions between S-Adenosylhomocysteine and the 5'-Alkylthio Binding Subsite", Biochemistry, 2012, vol. 51, Issue 48, pp. 9763-9772. (Year: 2012).*
Szöllősi et al. "Application of Fluorescence Resonance Energy Transfer in the Clinical Laboratory: Routine and Research", Communications in Clinical Cytometry, 1998, vol. 34, Issue 4, pp. 159-179. (Year: 1998).*

(Continued)

Primary Examiner — Louise W Humphrey
Assistant Examiner — Deepa Mishra
(74) Attorney, Agent, or Firm — Daniel H. Lajiness; Daniel F. Nesbitt; Nesbitt IP LLC

(57) ABSTRACT

Methods and kits for quantifying adenosine-containing molecules within an aqueous composition. Particularly, the methods utilize a competitive fluorescence-polarization and FRET-based assays that directly measure the production of adenosine-containing compounds, particularly S-adenosylhomocysteine (AdoHcy) compounds produced by MTases. The generation of AdoHcy can be quantified by displacing a novel fluorescent probe comprising a 5-carboxytetramethylrhodamine fluorophore covalently bound to an adenosine scaffold from a catalytically inert 5'-methylthioadenosine nucleosidase (MTAN) variant. One or more of the reaction materials can be pre-loaded into wells within multi-well reaction plates as a kit, which can be used to determine the enzymatic activity of MTases or conduct drug screening for potential inhibitors in a high-throughput format. Additionally, the developed assay is applicable to S-adenosyl methionine-dependent and adenosine triphosphate-dependent enzymes by detecting adenosine and various adenosine-containing molecules including 5'-methylthioadenosine, adenosine monophosphate and adenosine diphosphate produced during the course of a chemical reaction.

9 Claims, 12 Drawing Sheets
Specification includes a Sequence Listing.

(56) References Cited

OTHER PUBLICATIONS

Fernley et al., "Studies on Alkaline Phosphatase—Inhibition by Phosphate Derivatives and the Substrate Specificity", 1967, Biochem J., vol. 104, p. 1011-1018 (8 pages).
Zhang et al., "A Simple Statistical Parameter for Use in Evaluation and Validation of High Throughput Screening Assays", 1999, J. Biomol. Screening, vol. 4 No. 2, p. 67-73 (7 pages).
Cannon et al., "A stereospecific colorimetric assay for (S,S)-adenosylmethionine quantification based on thiopurine methyltransferase-catalyzed thiol methylation", Sep. 15, 2002, Anal. Biochem., vol. 308, p. 358-363 (6 pages).
Huang, "Fluorescence Polarization Competition Assay: The Range of Resolvable Inhibitor Potency is Limited by the Affinity of the Fluorescent Ligand", 2003, J. Biolmol. Screening, vol. 8 No. 1, p. 34-38 (5 pages).
Hendricks et al., "An enzyme-coupled colorimetric assay for S-adenosylmethionine-dependent methyltransferases", Mar. 2004, Anal. Biochem., vol. 326, p. 100-105 (6 pages).
Lee et al., "Mutational Analysis of a Nucleosidase Involved in Quorum-Sensing Autoinducer-2 Biosynthesis", 2005, Biochemistry, vol. 44, No. 33, p. 11049-11057 (9 pages).
Dorgan et al., "An enzyme-coupled continuous spectrophotometric assay for S-adenosylmethionine-dependent methyltransferases" Mar. 2006, Anal. Biochem., vol. 350 No. 2, p. 249-255 (6 pages).
Ishida et al., "Recent advances in technologies for analyzing protein kinases", Jan. 2007, J. Pharmacol. Sci., vol. 103, p. 5-11 (7 pages).
Kubicek et al., "Reversal of H3K9me2 by a Small-Molecule Inhibitor for the G9a Histone Methyltransferase", Feb. 2007, Mol. Cell, vol. 25 No. 3, p. 473-481 (9 pages).
Graves et al., "A universal competitive fluorescence polarization activity assay for S-adenosylmethionine utilizing methyltransferases", Feb. 2008, Anal. Biochem., vol. 373 No. 2, p. 296-306 (11 pages).
Li et al., "Evaluation of an antibody-free ADP detection assay: ADP-Glo", Dec. 2009, Assay Drug Dev. Technol., vol. 7, p. 598-605 (8 pages).
Quinn et al., "A chemiluminescence-based method for identification of histone lysine methyltransferase inhibitors", 2010, Mol. Biosyst., vol. 6, p. 782-788 (PMC manuscript—12 pages).
Lea et al., "Fluorescence Polarization Assays in Small Molecule Screening", Jan. 2011, Expert Opin. Drug Discov., 6(1), p. 17-32 (25 pages).
Klink et al., "Development and validation of a generic fluorescent methyltransferase activity assay based on the transcreener AMP/GMP assay", Jan. 2012, J. Biomol. Screening, vol. 17, p. 59-70 (12 pages).
Luo, "Current chemical biology approaches to interrogate protein methyltransferases", Mar. 2012, ACS Chem. Biol., vol. 7, p. 443-463 (PMC manuscript—39 pages).
Mishra et al., "Crystal structures of the Helicobacter pylori MTAN enzyme reveal specific interactions between S-adenosylhomocysteine and the 5'-alkylthio binding subsite", Dec. 2012, ACS Biochem., vol. 51, p. 9763-9772 (PMC manuscript—20 pages).
Thermo Scientific, "Crosslinking Technical Handbook", 2012 (56 pages).
Drake et al., "A sensitive luminescent assay for the histone methyltransferase NSD1 and other SAM-dependent enzymes", Jun. 2014, Assay Drug Dev. Technol., vol. 12, p. 258-271 (14 pages).
Jeong et al., "Structural insights into the histidine trimethylation activity of EgtD from *Mycobacterium smegmatis*", Oct. 2014, Biochem. Biophys. Res. Commun., vol. 452, p. 1098-1103 (7 pages).
Brown et al., "Using S-adenosyl-L-homocysteine capture compounds to characterize S-adenosyl-L-methionine and S-adenosyl-L-homocysteine binding proteins", Dec. 2014, Anal. Biochem., vol. 467, p. 14-21 (PMC manuscript—20 pages).
Yi et al., "Structure-guided DOT1L probe optimization by label-free ligand displacement", Mar. 2015, ACS Chem. Biol., vol. 10, p. 667-674 (8 pages).
Banco Michael et al. (2015), Neutron/X-ray Joint Refinement of the Active and Inactive Form of Helicobacter Pylori 5'-Methylthioadenosine Nucleosidase, Biosciences Information Services, PA, Database Biosis (online), vol. 29, No. Suppl. 1, Apr. 2015, (p. 572.16), Experimental Biology Meeting 2015, Boston, MA, Mar. 28-Apr. 1, 2015 (abstract—1 page).
Tekpinar et al., "Molecular Dynamics Study of the Effect of Active Site Protonation on Helicobacter Pylori5'-methylthioadenosine/S-adenosylhomocysteine Nucleosidase", Dec. 2015, Eur Biophys. J, vol. 44, No. 8 , p. 685-696.
Ronning et al., "The development of fluorescent probes to assess enzymatic activity of adenosine metabolism in vitro", 2015, Poster Presentation, Univ. Toledo (1 page).
Banco et al. "Neutron Structures of the Helicobacter Pylori 5'-Methylthioadenosine Nucleosidase Highlight Proton Sharing and Protonation States", Nov. 2016, PNAS USA, vol. 113, No. 48, p. 13756-13761 (6 pages).
Firestone et al., "Continuous Fluorescence Assays for Reactions Involving Adenine", Dec. 2016, Anal. Chem., vol. 88, p. 11860-11867 (PMC manuscript—22 pages).
Ahn et al., "A New s-adenosylhomocysteine Hydrolase-linked Method for Adenosine Detection Based on DNA-templated Fluorescent Cu/Ag Nanoclusters", Jul. 2017, Biosens. Bioelectron., vol. 93, p. 330-334 (5 pages).
International Search Report and Written Opinion dated Jul. 5, 2019 in corresponding International Application No. PCT/US2018/066817 filed Dec. 20, 2018 (12 pages).
International Preliminary Report on Patentability (Chapter I), dated Jul. 2, 2020 in corresponding International Application No. PCT/US2018/066817 filed Dec. 20, 2018 (8 pages).

\* cited by examiner

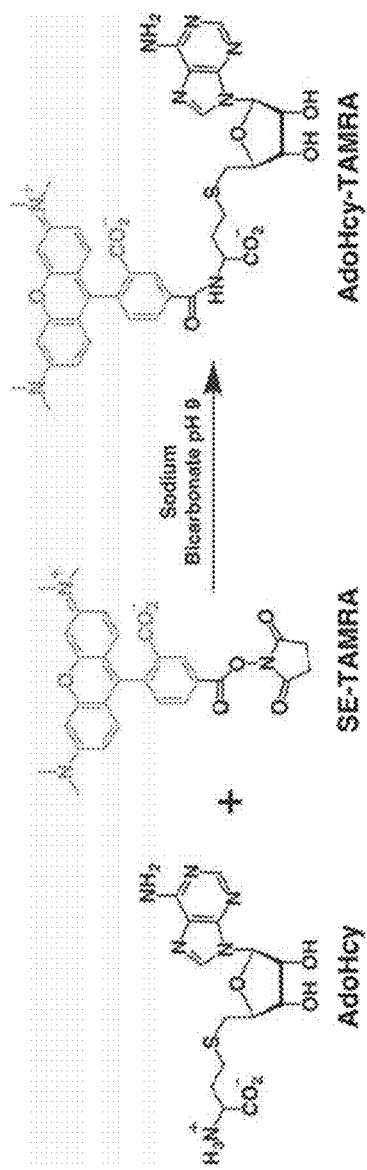
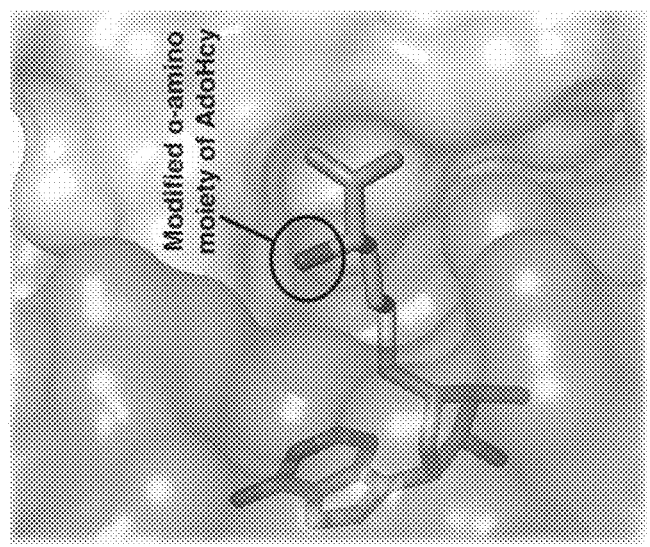
FIG. 2
FIG. 3

METHODS AND KITS FOR QUANTIFYING ADENOSINE-CONTAINING MOLECULES

CROSS-REFERENCE TO RELATED APPLICATIONS

The present application is the National Stage of International Application No. PCT/US2018/066817 filed Dec. 20, 2018, which claims the benefit of U.S. Provisional Application No. 62/608,011, filed Dec. 20, 2017, the disclosures of which are incorporated herein by reference in their entireties.

FIELD OF THE INVENTION

The present invention is in the field of biochemical assays for quantifying adenosine and adenosine-containing compounds.

REFERENCE TO SEQUENCE LISTING

The present application is being filed along with a sequence listing in electronic format. The sequence listing is provided as a file entitled "DRR-001M PCT Sequence Listing.txt" created on Dec. 20, 2018 and which is 13,628 bytes in size. The information in electronic format of the sequence listing is incorporated by reference in its entirety.

BACKGROUND OF THE INVENTION

S-adenosyl methionine (AdoMet) serves as an essential substrate for a myriad of transfer reactions in bacteria, archaea, and eukaryotes, which include post-translational modification of proteins, epigenetic regulation, polyamine biosynthesis, radical pathways, and quorum sensing. In this role, AdoMet is the second most widely used metabolite as a cofactor for enzymatic reactions following ATP. AdoMet-dependent methyltransferases (MTases) are the diverse class of enzymes that assist in the methylation of numerous biomolecular components in cells from all 3 domains of life. MTases catalyze the transfer of a methyl group from AdoMet to an acceptor molecule, generating S-adenosylhomocysteine (AdoHcy) and the modified methylated molecule. Additionally, products generated from AdoMet-dependent enzymes including AdoHcy, 5'-methylthioadenosine (MTA), and 5'-deoxyadenosine are known potent inhibitors of enzymes that catalyze methylation reactions, polyamine biosynthesis and AdoMet radical pathways, respectively. In some bacteria, the cellular concentrations of products from AdoMet-dependent enzymes are catabolized by MTA/AdoHcy nucleosidase (MTAN) to avoid product inhibition of these vital biochemical processes. Additionally, undesired methylation by MTases in humans leads to epigenetic dysregulation of transcription, which is demonstrated to play an important role in carcinogenesis. More specifically, alterations in the methylation of histones and DNA by MTases result in chromosomal instability and spurious gene expression, consequently leading to tumorigenesis. Furthermore, methylation of A2058 of 23S rRNA in the large subunit of the *Escherichia coli* ribosome by MTases have been shown to promote intrinsic resistant to three distinct classes of antibiotics including macrolides, lincosamides and quinupristin. For these reasons, there is great interest in enzymatic characterization of MTase function as well as development of novel inhibitors for MTases. Such compounds could be used as antimicrobials or anti-cancer therapeutics.

Various methods have been developed to directly and indirectly monitor the activity of MTases, but these lack sensitivity, exhibit inefficiency in medium to high throughput screening, or require radioisotopic labeling of substrates. Several of these assays are dependent on multiple coupled enzymes to process the generated AdoHcy product into a chromophore or luminophore (See Hendricks, C. L., et al., *Anal. Biochem.* 2004, 326, 100-105; Ibanez, G., et al., *Anal. Biochem.* 2010, 401, 203-210; and Dorgan, K. M., et al., *Anal. Biochem.* 2006, 350, 249-255). Early-developed spectroscopic kinetic methods for MTases exhibit inherently low sensitivity when detecting AdoHcy, which becomes problematic for performing kinetic analyses on catalytically slow enzymes. Alternatively, luminescence-based assays developed for MTases have demonstrated to be highly sensitive for detecting generated AdoHcy (See Jiang, C., et al., *Anal. Biochem.* 2012, 423, 224-228; and Drake, K. M., et al., *Assay Drug Dev. Technol.* 2014, 12, 258-271). An inherent challenge of efficiently screening small molecule libraries with coupled enzymes is the elevated hit rate of false positives and the requirement for orthogonal assays to validate hits.

Assays that directly measure AdoHcy or methylated products improve the adaptability for high-throughput screening by potentially reducing the hit rate of false positives. Immuno-based assays that directly detect methylated histone products have been demonstrated to be feasible for medium to high-throughput screening by successfully identifying inhibitors. For example, such assays have identified inhibitors targeting a G9a MTase, which is a eukaryotic histone lysine MTase (See Luo, M. *ACS Chem. Biol.* 2012, 7, 443-463; Kubicek, S., et al., *Mol. Cell* 2007, 25, 473-481; and Quinn, A. M., et al., *Mol. Biosyst.* 2010, 6, 782-788). Conversely, detecting AdoHcy rather than specific methylated products provides a universal detection mechanism that can be applied to any MTase. For instance, fluorescence polarization (FP) is a widely-used technique that monitors the fractional binding of a fluorescently labeled ligand to an enzyme. Graves and co-workers previously developed a competitive FP immunoassay for detecting generated AdoHcy from MTases, which differentiates AdoHcy from background AdoMet and exhibits a LOD of 0.5 pmol of AdoHcy (see Graves, T. L., et al., *Anal. Biochem.* 2008, 373, 296-306). Although direct immunodetection of AdoHcy provides several advantages for high-throughput screening of small-molecule libraries, production of high-titer antibodies can be prohibitively expensive.

Consequently, there is still a need to develop new assays for monitoring the activity of MTases that are highly sensitive, cost-effective, and suitable for high-throughput screening of potential small molecule inhibitors.

SUMMARY OF THE INVENTION

The present disclosure includes methods and kits that can be used to quantify adenosine-containing compounds within a solution. In some embodiments, the methods of the present invention can be used to quantify adenosine-containing compounds that are formed from chemical reactions catalyzed by certain enzymes, particularly S-adenosyl methionine (AdoMet) dependent enzymes and adenosine triphosphate (ATP) dependent enzymes. In further embodiments, adenosine-containing compounds are quantified in real-time.

In a first embodiment, the concentration of adenosine-containing compounds within an aqueous composition can be determined by displacing a fluorescent probe complexed within the inactivated active site of a mutated, 5'-methylthioadenosine/S-adenosylhomocysteine nucleosidase (MTAN) enzyme, causing a quantifiable change in the fluorescence properties of the probe as it is released into the aqueous composition. In some embodiments, the change in fluorescence polarization or anisotropy of the fluorescent probe can be measured as an adenosine-containing compound disrupts the complex between the mutant MTAN enzyme and the fluorescent probe and binds within the active site. In other embodiments, the difference in the fluorescence resonance energy transfer (FRET) between the fluorescent probe and a second fluorophore crosslinked to a cysteine residue within the mutant MTAN enzyme can be measured as an adenosine-containing compound disrupts the complex between the mutant MTAN enzyme and the fluorescent probe and binds within the active site. Adenosine-containing compounds that can be quantified using methods of the present invention include, but are not limited to, S-adenosylhomocysteine (AdoHcy), 5'-methylthioadenosine (MTA), adenosine diphosphate (ADP), adenosine monophosphate (AMP), and adenosine. In further embodiments, the adenosine-containing compound that can be quantified using methods of the present invention is AdoHcy.

In another embodiment, the fluorescent probe comprises an adenosine scaffold comprising an adenine moiety and a ribosyl moiety and a 5-carboxytetramethylrhodamine (TAMRA) fluorophore. In further embodiments, the TAMRA fluorophore is covalently bound to the adenosine scaffold by a linking portion comprising a linear chain of six or more atoms extending from the 5'-carbon of the ribosyl moiety to the 5-carboxyl functional group within TAMRA.

In another embodiment, the adenosine scaffold is S-adenosylhomocysteine (AdoHcy), and the 5-carboxyl functional group within TAMRA is covalently bound to the α-amino moiety within AdoHcy. In further embodiments, the fluorescent probe comprising AdoHcy as the adenosine scaffold can be synthesized in a one-pot synthesis by incubating AdoHcy with a 5-carboxytetramethylrhodamine succinimidyl ester (SE-TAMRA). The resulting AdoHcy-TAMRA fluorophore can be purified and stored prior to use in an assay to quantify the presence and/or production of adenosine-containing compounds.

In another embodiment, the fluorescent probe forms a protein-probe complex with an inactivated MTAN enzyme in which one or more active site residues are mutated in order to prevent MTAN's native nucleosidase activity upon binding with an adenosine-containing compound and/or the fluorescent probe itself. In further embodiments, the enzyme is inactivated by mutating the catalytic aspartic acid residue within the active site, a common feature found in all known bacterial MTAN enzymes, to an asparagine residue. In even further embodiments, the mutated MTAN enzyme within the protein probe complex can comprise the entirety or a portion of the amino acid sequence of any of the enzymes within Enzyme Class (EC) 3.2.2.9, all of which have been identified to have MTAN activity and which have a universally conserved active site aspartic acid residue.

In another embodiment of the invention, the amino acid sequence of the mutated MTAN enzyme is derived from the native enzyme found in *Helicobacter pylori* (Hp), the nucleic acid sequence of which is disclosed as SEQ ID NO: 3. In further embodiments, the mutated enzyme comprises an aspartic acid to asparagine mutation at position 198 (D198N). In even further embodiments, the mutated MTAN enzyme within the protein-probe complex comprises the amino acid sequence of SEQ ID NO: 1.

In another embodiment of the invention, mutated MTAN enzymes that comprise the protein-probe complexes utilized in accordance with methods of the present invention have the ability to bind with AdoMet in addition to the adenosine-containing compounds listed above. Typically, reactions that produce AdoHcy, MTA, ADP, AMP, and adenosine utilize AdoMet as the starting material—however, AdoMet can also bind within the active site of the mutated MTAN enzyme and disrupt the interaction between the fluorescent probe and the enzyme.

Thus, in another embodiment, the amino acid sequence of the MTAN-D198N enzyme can be further mutated at positions that surround the thioether functionality of AdoMet when it is bound within the active site, in order to reduce or eliminate the binding affinity of the mutated MTAN toward AdoMet without affecting the ability of the enzyme to bind with other adenosine-containing compounds, particularly AdoHcy. In further embodiments, at least one mutation can be engineered into at least one of four positions within SEQ ID NO: 1, Ile-52, Leu-104, Phe-153, and Met-174. In even further embodiments, the resulting mutated MTAN enzyme comprises the amino acid sequence of SEQ ID NO: 8, which contains residues having the designation, "Xaa," which illustrates known instances in which the amino acid at that position can be selected from a group of two or more amino acids.

In another embodiment, at least one of the natural amino acid residues at position 52, position 104, position 153, and position 174 can be mutated to any other amino acid residue through random mutagenesis. In other embodiments, at least one of the natural amino acid residues at position 52, position 104, position 153, and position 174 can be conservatively mutated to either a sterically bulky amino acid residue, including but not limited to methionine, or a positively-charged residue, including but not limited to arginine. In further embodiments, within mutated MTAN enzymes comprising the amino acid sequence of SEQ ID NO: 8, the residue at X52 is either isoleucine, methionine, or arginine. In other further embodiments, within mutated MTAN enzymes comprising the amino acid sequence of SEQ ID NO: 8, the residue at X104 is either leucine, methionine, or arginine. In still other further embodiments, within mutated MTAN enzymes comprising the amino acid sequence of SEQ ID NO: 8, the residue at X153 is phenylalanine or arginine. In yet still other further embodiments, within mutated MTAN enzymes comprising the amino acid sequence of SEQ ID NO: 8, the residue at X174 is methionine or arginine.

In another embodiment, the amino acid sequence of the MTAN-D198N enzyme can further comprise a mutation to a cysteine residue at one or more positions on the periphery of the enzyme that are within less than about 20 Å from the α-amino group of the AdoHcy moiety when the fluorescent probe is bound within the active site. For example, the mutated cysteine residue can be located less than about 18, 16, 14, 12, 10, 8 Å, or 6 Å from the α-amino group of the AdoHcy moiety when the fluorescent probe is bound within the active site. In other embodiments, the amino acid sequence of the MTAN-D198N enzyme can further comprise a mutation to a cysteine residue at one or more positions on the periphery of the enzyme that are within at least 6 Å from the α-amino group of the AdoHcy moiety when the fluorescent probe is bound within the active site. For example, the mutated cysteine residue can be located at least about 8, 10, 12, 14, 16, or 18 Å, up to at least about 20 Å from the α-amino group of the AdoHcy moiety when the fluorescent probe is bound within the active site. In some further embodiments, the mutated MTAN enzyme further comprises a glutamic acid to cysteine mutation at position 12. In even further embodiments, the mutated MTAN enzyme comprises the amino acid sequence of SEQ ID NO: 4. In other further embodiments, the mutated MTAN enzyme further comprises a glutamic acid to cysteine mutation at position 213. In even further embodiments, the mutated MTAN enzyme comprises the amino acid sequence of SEQ ID NO: 6.

Within mutated MTAN enzymes that further comprise one or more peripheral mutations to a cysteine residue, the cysteine residue can then be further conjugated to a secondary fluorophore comprising a fluorescently-active moiety and a thiol-reactive crosslinker that bridges the fluorescently-active moiety to the cysteine residue. In some embodiments, within enzymes comprising the amino acid sequence of SEQ ID NO: 4, Cys-12 is conjugated to the secondary fluorophore. In further embodiments, the amino acid at position 12 within SEQ ID NO: 8 is selected to be a cysteine residue, and Cys-12 is conjugated to the secondary fluorophore. In other embodiments, within enzymes comprising the amino acid sequence of SEQ ID NO: 6, Cys-213 is conjugated to the secondary fluorophore. In further embodiments, the amino acid at position 213 within SEQ ID NO: 8 is selected to be a cysteine residue, and Cys-213 is conjugated to the secondary fluorophore.

In embodiments in which Cys-12 or Cys-213 is conjugated to a secondary fluorophore, the thiol-reactive crosslinker comprises a functional group consisting of a haloacetyl, maleimide, or vinyl amide group. In even further embodiments, the thiol-reactive crosslinker comprises a maleimide group.

The present invention also provides several nucleic acid sequences that encode for the mutated MTAN enzymes described above. In another embodiment, the nucleic acid sequence can comprise any sequence encoding for a polypeptide comprising an amino acid sequence selected from the group consisting of SEQ ID NO: 1, SEQ ID NO: 4, SEQ ID NO: 6, and SEQ ID NO: 8, and complements thereof. In further embodiments, the nucleic acid sequence can be selected from the group consisting of SEQ ID NO: 2, SEQ ID NO: 5, and SEQ ID NO: 7, and complements thereof, which encode SEQ ID NO: 1, SEQ ID NO: 4, SEQ ID NO: 6, respectively.

In another embodiment, the gene comprising the nucleic acid sequence of SEQ ID NO: 2 can be formed by performing site-directed mutagenesis of the wild type *H. pylori* MTAN, comprising the nucleic acid sequence of SEQ ID NO: 3. In other embodiments, genes comprising the nucleic acid sequence of SEQ ID NO: 5 or SEQ ID NO: 7 can be formed by performing site-directed mutagenesis of the nucleic acid sequence of SEQ ID NO: 2 or SEQ ID NO: 3.

In another embodiment, any nucleic acid sequence encoding for a mutated MTAN enzyme of the present invention can be inserted into an expression vector that is engineered to be inserted into biological host cells configured to retain the expression vector and overexpress the desired enzyme. In some embodiments, the expression vector comprises any nucleic acid sequence encoding for an a mutated MTAN enzyme comprising an amino acid sequence selected from the group consisting of SEQ ID NO: 1, SEQ ID NO: 4, SEQ ID NO: 6, and SEQ ID NO: 8. In further embodiments, the vector comprises a nucleic acid sequence selected from the group consisting of SEQ ID NO: 2, SEQ ID NO: 5, and SEQ ID NO: 7.

In another embodiment, the expression vector can optionally further comprise one or more nucleic acid sequences or genes encoding for proteins or host recognition sites that supplement the production of mutated MTAN enzymes of the present invention. Non-limiting examples include promoter sequences, antibiotic resistance genes, and genes encoding for fusion proteins that assist in the folding and stability of the engineered enzyme, for example, the malE gene from *Escherichia coli*, which encodes for maltose binding protein.

In another embodiment, expression vectors are typically transformed into host cells from which the enzyme can be overexpressed and extracted. In some embodiments, host cells can be transformed with any of the expression vectors described above, particularly an expression vector comprising any nucleic acid sequence encoding for a mutated MTAN enzyme comprising an amino acid sequence selected from the group consisting of SEQ ID NO: 1, SEQ ID NO: 4, SEQ ID NO: 6, and SEQ ID NO: 8. In further embodiments, the expression vector comprises a nucleic acid sequence selected from the group consisting of SEQ ID NO: 2, SEQ ID NO: 5, and SEQ ID NO: 7.

In another embodiment, any host cell comprising an expression vector encoding for a mutated MTAN enzyme of the present invention can subsequently be isolated. In some embodiments, transformed and isolated host cells can be selected from the group consisting of bacterial cells, yeast cells, insect cells, or mammalian cells. In some embodiments, the transformed and isolated host cells are bacterial cells. In further embodiments and as a non-limiting example, the bacterial cells are *Escherichia coli* (*E. coli*) cells. In even further non-limiting embodiments, the *E. coli* are non-pathogenic.

In another embodiment, mutated MTAN enzymes expressed within a host cell may then be substantially isolated and purified from the cells by standard methods. Alternatively, the isolated nucleic acids of the invention may be used in cell-free in vitro translation systems to produce the mutated MTAN enzymes of the present invention. In further embodiments, a reducing agent, for example dithiothreitol or tris(2-carboxyethyl)phosphine (TCEP), can be included in aqueous compositions utilized during protein expression, purification, and/or storage in order to reduce or eliminate unwanted disulfide bonds between peripheral cysteine residues on one or more mutated MTAN polypeptides. In even further embodiments, the reducing agent is TCEP. In other even further embodiments, TCEP is included in any aqueous composition comprising a mutated MTAN enzyme having a Cys-12 or Cys-213 residue, including mutated MTAN enzymes comprising the amino acid sequence of SEQ ID NO: 4, SEQ ID NO: 6, and SEQ ID NO: 8.

In another embodiment, the present invention also provides substantially pure protein preparations comprising at least a functional fragment of a mutated MTAN enzyme. In a further embodiment, the present invention provides a substantially pure protein preparation in which the enzyme comprises a polypeptide comprising an amino acid sequence selected from the group consisting of SEQ ID NO: 1, SEQ ID NO: 4, SEQ ID NO: 6, and SEQ ID NO: 8.

The invention provides methods for quantifying of adenosine-containing compounds within an aqueous composition. In another embodiment, the method for quantifying adenosine-compounds utilizes a fluorescence polarization (FP) assay, in which a fluorescence polarization value or anisotropy value is determined for the fluorescent probe either in complex with a mutated MTAN enzyme of the present invention, or as a free molecule in an aqueous composition after an adenosine-containing compound has displaced the fluorescent probe from the inactivated MTAN active site. The difference in polarization or anisotropy of the fluorescent probe in the bound and unbound forms is then utilized to determine the concentration of the adenosine-containing compound in the aqueous composition. In further embodiments, the concentration of adenosine-containing compounds can be quantified in real time during chemical reactions in which adenosine-containing compounds are generated as a product.

In another embodiment, methods for quantifying adenosine-containing compounds within an aqueous composition comprise the steps of (a) providing a fluorescent probe comprising an adenosine scaffold comprising an adenine moiety and a ribosyl moiety, and a TAMRA fluorophore, wherein the adenosine scaffold is covalently bound to the fluorophore by a linking portion comprising a linear chain of six or more atoms extending from the 5'-carbon of the ribosyl moiety to the 5-carboxyl functional group within TAMRA; (b) providing a mutated MTAN enzyme, wherein the mutated MTAN enzyme comprises a mutation within the active site from an aspartic acid residue to an asparagine residue; (c) forming a protein-probe complex between the mutated MTAN enzyme and the fluorescent probe; (d) combining an adenosine-containing compound with the protein-probe complex to form an adenosine quantification mixture; (e) measuring the parallel fluorescence intensity and the perpendicular fluorescence intensity of the adenosine quantification mixture to determine a polarization value or anisotropy value; and (f) calculating the amount of the adenosine-containing compound within the adenosine quantification mixture using the measured polarization value or anisotropy value.

In another embodiment, the adenosine scaffold is AdoHcy, and the 5-carboxyl functional group of TAMRA is covalently bound to the α-amino moiety within AdoHcy. Accordingly, methods for quantifying of adenosine-containing compounds within an aqueous composition can comprise the steps of: providing an inactivated, MTAN-D198N enzyme; providing a fluorescent probe comprising an AdoHcy molecule amide-linked to a TAMRA fluorophore at the AdoHcy's α-amino position; forming a protein-probe complex between the MTAN-D198N and the fluorescent probe; combining a reaction mixture comprising an adenosine-containing compound with the protein-probe complex to form an adenosine quantification mixture; measuring the parallel fluorescence intensity and the perpendicular fluorescence intensity of the adenosine quantification mixture to determine a polarization value; and calculating the amount of the adenosine-containing compound within the adenosine quantification mixture using the measured polarization value.

In another embodiment, the quantity of the adenosine-containing compound within the adenosine quantification mixture can be determined directly by comparing the measured polarization value or anisotropy value to a standard curve that correlates the polarization value with known concentrations of the adenosine-containing compound. In other embodiments, the adenosine-containing compound is selected from the group consisting of AdoHcy, MTA, ADP, AMP, and adenosine.

In another embodiment, the method for quantifying adenosine-containing compounds within an aqueous composition utilizes a FRET assay, in which fluorescence by the fluorescent probe within an MTAN protein-probe complex in the presence of a covalently cross-linked secondary fluorophore is compared against the fluorescence of the unbound fluorescent probe. The difference in the fluorescence of the fluorescent probe in the bound and unbound forms is then utilized to determine the concentration of the adenosine-containing compound in the aqueous composition. Similar to FP assay methods of the present invention, the quantity of adenosine-containing compounds can be quantified using FRET methods of the present invention in real time during chemical reactions in which adenosine-containing compounds are generated as a product. In further embodiments, covalently cross-linked secondary fluorophores are crosslinked to cysteine residues that have been engineered into the D198N-MTAN enzyme. In even further embodiments, the mutated MTAN enzyme comprises a Cys-12 residue cross- and comprises the amino acid sequence of either SEQ ID NO: 4 or SEQ ID NO: 8. In other even further embodiments, the enzyme comprises a Cys-213 residue and comprises the amino acid sequence of either SEQ ID NO: 6 or SEQ ID NO: 8. In still further embodiments, the secondary fluorophore cross-linked to either Cys-12 or Cys-213 comprises an absorption wavelength that overlaps with an emission wavelength of TAMRA.

In another embodiment, methods for quantifying adenosine-containing compounds in an aqueous composition using FRET comprise the steps of: (a) providing a fluorescent probe comprising an adenosine scaffold comprising an adenine moiety and a ribosyl moiety, and a TAMRA fluorophore, wherein the adenosine scaffold is covalently bound to the fluorophore by a linking portion comprising a linear chain of six or more atoms extending from the 5'-carbon of the ribosyl moiety to the 5-carboxyl functional group within TAMRA; (b) providing a mutated MTAN enzyme, wherein the mutated MTAN enzyme comprises (i) an amino acid sequence selected from the group consisting of SEQ ID NO: 4, SEQ ID NO: 6, and SEQ ID NO: 8, and (ii) a cysteine residue that is conjugated to a secondary fluorophore comprising a fluorescently-active moiety and a thiol-reactive crosslinker that bridges the fluorescently-active moiety to the cysteine residue; (c) forming a protein-probe complex between the mutated MTAN enzyme and the fluorescent probe; (d) measuring the fluorescence intensity of the fluorescent probe within the protein-probe complex; (e) combining an adenosine-containing compound with the protein-probe complex to form an adenosine quantification mixture; (f) measuring the increase of fluorescence intensity of the fluorescent probe in the presence of the adenosine quantification mixture; and calculating the amount of the adenosine-containing compound within the adenosine quantification mixture using the increase of fluorescence intensity of the fluorescent probe in the presence of the adenosine quantification mixture.

In another embodiment, any of the methods described above can further comprise the step of synthesizing the fluorescent probe, the synthesis comprising the steps of: incubating AdoHcy with a stoichiometric amount of SE-TAMRA and initiating a nucleophilic attack of the succinimidyl ester within SE-TAMRA by the nucleophilic α-amino group of AdoHcy, thereby forming an amide linkage between TAMRA and AdoHcy. In further embodiments, AdoHcy and SE-TAMRA are incubated for at least 10 minutes, including at least 15, 20, 25, or 30 minutes, up to at least 60 minutes. In other further embodiments AdoHcy and SE-TAMRA are incubated for less than 60 minutes, including less than 30, 25, 20, or 15 minutes, down to less than 10 minutes.

In another embodiment, methods of the present invention that utilize FP to quantify adenosine-containing compounds can comprise an amino acid sequence selected from the group consisting of SEQ ID NO: 1, SEQ ID NO: 4, SEQ ID NO: 6, and SEQ ID NO: 8.

In another embodiment, methods of the present invention that utilize FRET to quantify adenosine-containing compounds can comprise the amino acid sequence of SEQ ID NO: 4 or SEQ ID NO: 8, wherein the amino acid residue at position 12 is a cysteine residue, and the Cys-12 residue is conjugated to the cross-linked secondary fluorophore. In other embodiments, methods of the present invention that utilize FRET to quantify adenosine-containing compounds can comprise the amino acid sequence of SEQ ID NO: 6 or SEQ ID NO: 8, wherein the amino acid residue at position 213 is a cysteine residue, and the Cys-213 residue is conjugated to the cross-linked secondary fluorophore. In further embodiments, the crosslinker that covalently links the secondary fluorophore to the cysteine residue comprises a functional group selected from the group consisting of a haloacetyl, maleimide, or vinyl amide group. In even further embodiments, the crosslinker comprises a maleimide group.

In another embodiment, any of the methods of the present invention can further comprise the steps of synthesizing the adenosine-containing compound by combining within a reaction mixture at least one supplemental enzyme and at least one supplemental starting material that react to form an adenosine-containing compound as a product, and combining the reaction mixture containing the adenosine-containing compound product with the protein-probe complex. In further embodiments, the at least one supplemental enzyme includes an enzyme selected from the group consisting of an AdoMet-dependent enzyme and an ATP-dependent enzyme. In even further embodiments, the rate of the adenosine-containing compound formed as part of the reaction can be used to determine kinetic parameters for the enzymatic reaction, including but not limited to $k_{cat}$, $K_m$, and $K_m^{app}$.

In another embodiment, the reaction mixture comprises a methyltransferase enzyme and AdoMet as a supplemental starting material, wherein the concentration of the AdoMet within the reaction mixture is less than about 5 µM, including less than about 2.5 µM. In other embodiments, the reaction mixture comprises an ATP-dependent enzyme and ATP as a supplemental starting material, wherein the ATP-dependent enzyme is an ATP-dependent kinase. In further embodiments, effect of the contribution of reaction starting materials, particularly AdoMet and ATP, can be determined and subtracted out as background.

In another embodiment, the reaction mixture can further comprise at least one small-molecule inhibitor candidate, preferably a small-molecule inhibitor candidate having a molecular weight of less than about 1,000 Daltons. For example, the small-molecule inhibitor candidate can have a molecular weight of less than about 900, 800, 700, 600, 500, 400, 300, or 200 Daltons, down to less than about 100 Daltons. In other embodiments, the small-molecule inhibitor candidate is at least about 100 Daltons. For example, the small-molecule inhibitor candidate can have a molecular weight of at least about 200, 300, 400, 500, 600, 700, 800, or 900 Daltons, up to at least about 1,000 Daltons.

The invention also provides kits for quantifying adenosine-containing compounds. In another embodiment, kits for quantifying adenosine-containing compounds within an aqueous composition or reaction mixture can comprise: (a) a fluorescent probe comprising an adenosine scaffold comprising an adenine moiety and a ribosyl moiety, and a TAMRA fluorophore, wherein the adenosine scaffold is covalently bound to the fluorophore by a linking portion comprising a linear chain of six or more atoms extending from the 5'-carbon of the ribosyl moiety to the 5-carboxyl functional group within TAMRA; and (b) a mutated MTAN enzyme, wherein the mutated MTAN enzyme comprises a mutation within the active site from an aspartic acid residue to an asparagine residue. In further embodiments, the mutated MTAN enzyme comprises an amino acid sequence selected from the group consisting of SEQ ID NO: 1, SEQ ID NO: 4, SEQ ID NO: 6, and SEQ ID NO: 8. In other further embodiments, the adenosine scaffold is AdoHcy, and the 5-carboxyl functional group of TAMRA is covalently bound to the α-amino moiety within AdoHcy. In even further embodiments, the kit comprises an MTAN-D198N enzyme comprising the amino acid sequence of SEQ ID NO: 1, and a fluorescent probe comprising an AdoHcy molecule amide-linked to a TAMRA fluorophore at the AdoHcy's α-amino position.

In another embodiment, the fluorescent probe and a mutated MTAN enzyme comprising an amino acid sequence selected from the group consisting of SEQ ID NO: 1, SEQ ID NO: 4, SEQ ID NO: 6, and SEQ ID NO: 8 are provided together within the kit as a pre-formed, protein-probe complex. In other embodiments, the fluorescent probe and a mutated MTAN enzyme comprising an amino acid sequence selected from the group consisting of SEQ ID NO: 1, SEQ ID NO: 4, SEQ ID NO: 6, and SEQ ID NO: 8 are provided within separate compositions that are combined to form the protein-probe complex by a user prior to quantifying adenosine-containing compounds within an aqueous composition or reaction mixture.

In another embodiment, the kit comprises components for use with any FRET-based methods of the present invention for quantifying adenosine-containing compounds, including mutated MTAN enzymes comprising the amino acid sequence of SEQ ID NO: 4, SEQ ID NO: 6, and/or SEQ ID NO: 8. The mutated MTAN enzyme comprises a cysteine residue at either position 12 or 213 within the amino acid sequence is conjugated to a thiol-reactive secondary fluorophore comprising a fluorescently-active moiety and a crosslinker that bridges the fluorescently-active moiety to the cysteine residue. The crosslinker that connects the secondary fluorophore to the cysteine residue can include any of the functional groups described above, particularly a maleimide group.

In another embodiment, the kit further comprises at least one small-molecule inhibitor candidate, as described above. In further embodiments, each small-molecule inhibitor candidate is an organic compound. In even further embodiments, each small-molecule inhibitor candidate has a molecular weight of less than about 1,000 Daltons, including less than about 900, 800, 700, 600, 500, 400, 300, or 200 Daltons, down to less than about 100 Daltons. In other embodiments, the small-molecule inhibitor candidate has a molecular weight of at least about 100 Daltons, including at least about 200, 300, 400, 500, 600, 700, 800, or 900 Daltons, up to at least about 1,000 Daltons.

In another embodiment, kits can be especially useful for monitoring the production of adenosine-containing compounds during AdoMet-dependent or ATP-dependent reactions, particularly multiple reactions that are conducted simultaneously within a single plate or tray. In further embodiments, kit components are provided within a microplate configured for use with a fluorescence-detection instrument, the microplate comprising at least 1 well, including at least 6, 12, 24, 48, 96, or 384 wells, up to at least 1536 wells. In even further embodiments, each well within the microplate comprises at least one component selected from the group consisting of the fluorescent probe, the mutated MTAN enzyme, a protein-probe complex, and a small-molecule inhibitor candidate. In still further embodiments, for microplates in which each well comprises a small-molecule inhibitor candidate, each well contains the same small-molecule inhibitor candidate. In other still further embodiments, each well contains a different small-molecule inhibitor candidate.

BRIEF DESCRIPTION OF THE FIGURES

FIG. 2 shows a surface model of the inactivated MTAN enzyme complexed with S-adenosyl homocysteine.

FIG. 3 shows the synthetic scheme for AdoHcy-TAMRA.

DETAILED DESCRIPTION OF THE INVENTION

Figure 1A:
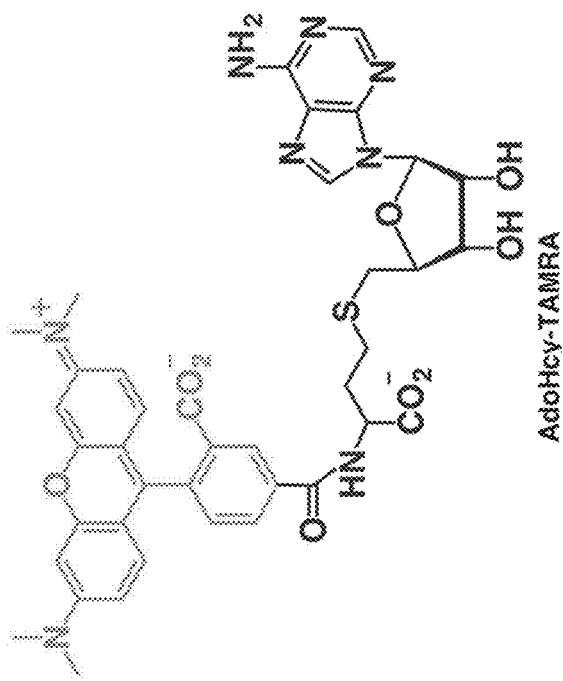
FIG. 1A shows the chemical structure of a fluorophore coupled to S-adenosyl homocysteine.

It should be understood that while reference is made to exemplary embodiments and specific language is used to describe them, no limitation of the scope of the invention is intended. Further modifications of the methods and system described herein, as well as additional applications of the principles of those inventions as described, which would occur to one skilled in the relevant art and having possession of this disclosure, are to be considered within the scope of this invention. Unless defined otherwise, all technical and scientific terms used herein have the same meaning as commonly understood by one of ordinary skill in the art to which embodiments of this particular invention pertain. The terminology used is for the purpose of describing those embodiments only, and is not intended to be limiting unless specified as such.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

The contents of all references mentioned in this specification are hereby incorporated by reference, and shall not be construed as an admission that such reference is available as prior art to the present invention. All of the incorporated publications and patent applications in this specification are indicative of the level of ordinary skill in the art to which this invention pertains, and are incorporated to the same extent as if each individual publication or patent application was specifically indicated and individually indicated by reference. The invention is further illustrated by the following working and prophetic examples, neither of which should be construed as limiting the invention. Additionally, to the extent that section headings are used, they should not be construed as necessarily limiting. Any use of the past tense to describe an example otherwise indicated as constructive or prophetic is not intended to reflect that the constructive or prophetic example has actually been carried out.

The present disclosure includes methods and kits that can be used to quantify adenosine-containing compounds within a solution. In some embodiments, the methods of the present invention can be used to quantify adenosine-containing compounds that are formed from chemical reactions catalyzed by certain enzymes, particularly S-adenosyl methionine (AdoMet) dependent enzymes and adenosine triphosphate (ATP) dependent enzymes. In further embodiments, adenosine-containing compounds are quantified in real-time.

Non-limiting examples of adenosine-containing compounds that can be quantified include S-adenosylhomocysteine (AdoHcy), 5'-methylthioadenosine (MTA), adenosine diphosphate (ADP), adenosine monophosphate (AMP), and adenosine. In some embodiments, the method quantifies the amount of AdoHcy produced by AdoMet-dependent methyltransferases (MTases). The methods and kits described herein have several advantages over conventional quantification methods of adenosine-containing compounds, particularly increased sensitivity, cost-effectiveness, and suitability for high-throughput screening, as well as reduced background interference with other components in a reaction mixture.

Each of the methods and kits of the present invention that are utilized to assess and quantify the presence of adenosine-containing compounds within an aqueous composition or reaction mixture comprises a unique fluorescent probe that has a strong binding affinity for an inactivated nucleosidase enzyme that has a promiscuous ability to bind to each of the adenosine-containing compounds described above. Suitable fluorescent probes that can be utilized in the present invention include fluorophores that are attached to an adenosine scaffold via the 5'-carbon of the ribosyl moiety within the adenosine scaffold. Such fluorophores are described in detail below.

In some embodiments, methods for quantifying adenosine-containing compounds within an aqueous composition comprise a fluorescence polarization (FP) assay comprising the steps of: (a) providing a fluorescent probe comprising an adenosine scaffold comprising an adenine moiety and a ribosyl moiety, and a 5-carboxytetramethylrhodamine (TAMRA) fluorophore, wherein the adenosine scaffold is covalently bound to the fluorophore by a linking portion comprising a linear chain of six or more atoms extending from the 5'-carbon of the ribosyl moiety to the 5-carboxyl functional group within TAMRA; (b) providing a mutated 5'-methylthioadenosine nucleosidase (MTAN) enzyme, wherein the mutated MTAN enzyme comprises a mutation within the active site from an aspartic acid residue to an asparagine residue; (c) forming a protein-probe complex between the mutated MTAN enzyme and the fluorescent probe; (d) combining an adenosine-containing compound with the protein-probe complex to form an adenosine quantification mixture; (e) measuring the parallel fluorescence intensity and the perpendicular fluorescence intensity of the adenosine quantification mixture to determine a polarization value or anisotropy value; and (f) calculating the amount of the adenosine-containing compound within the adenosine quantification mixture using the measured polarization value or anisotropy value.

In another embodiment, the adenosine scaffold is AdoHcy, and the 5-carboxyl functional group of TAMRA is covalently bound to the α-amino moiety within AdoHcy (AdoHcy-TAMRA), and methods for quantifying of adenosine-containing compounds within an aqueous composition can comprise the steps of: providing a mutated MTAN enzyme comprising the amino acid sequence of SEQ ID NO: 1; providing a fluorescent probe comprising an AdoHcy molecule amide-linked to a TAMRA fluorophore at the AdoHcy's α-amino position; forming a protein-probe complex between the mutated enzyme and the fluorescent probe; combining a reaction mixture comprising an adenosine-containing compound with the protein-probe complex to form an adenosine quantification mixture; measuring the parallel fluorescence intensity and the perpendicular fluorescence intensity of the adenosine quantification mixture to determine a polarization value; and calculating the concentration of the adenosine-containing compound within the adenosine quantification mixture using the measured polarization value.

MTAN enzymes that comprise the ability to bind with a variety of adenosine-containing compounds are comprised within Enzyme Class (EC) 3.2.2.9. The primary activity of the enzymes within EC 3.2.2.9 comprises the catalysis of the chemical reaction:

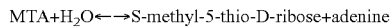

MTA+H$_2$O←→S-methyl-5-thio-D-ribose+adenine

However, wild type MTAN enzymes have the ability to catalyze the hydrolysis of N-ribosidic bonds of at least four different adenosine-based substrates: AdoHcy, MTA, 5'-deoxyadenosine (5'-DOA), and 6-amino-6-deoxyfutalosine. This hydrolytic activity places MTAN at the hub of at least seven fundamental metabolic pathways: the purine salvage pathway, the methionine salvage pathway, AdoMet-dependent methylation pathways, polyamine biosynthesis, the production of quorum sensing molecules and menaquinone biosynthesis. *Campylobacter* and *Helicobacter* are dependent on MTAN for menaquinone synthesis, an essential metabolite for bacterial viability. Without being limited by a particularly theory, the promiscuous ability of MTAN to interact with so many different small molecules enables the enzyme to successfully bind with TAMRA fluorophores attached to an adenosine scaffold.

However, using a wild type MTAN as a basis for the fluorescence-based methods of the present invention is not possible because the enzyme would be capable of catalytic turnover in the presence of an adenosine-based scaffold, particularly AdoHcy. Among the known native MTAN enzymes within EC 3.2.2.9, every enzyme contains a conserved aspartic acid residue within the active site that initiates catalysis. As a result, an inactivated version of the enzyme in which the catalytic aspartic acid residue within the active site is mutated to an asparagine enables AdoHcy and other adenosine-containing compounds to bind within the active site without initiating catalytic turnover. Thus, in another embodiment, the methods and kits of the invention can utilize any MTAN enzyme in which the conserved active site aspartic acid residue is mutated to an asparagine residue.

Figure 1B:
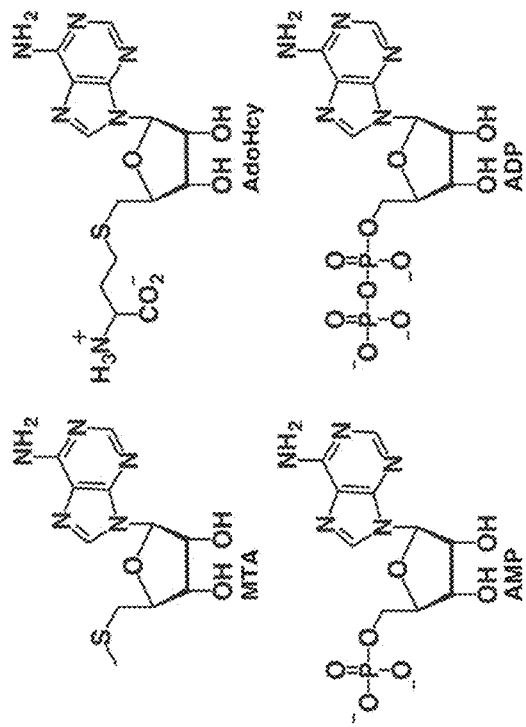
FIG. 1B shows the chemical structures of examples of adenosine-containing structures that can be quantified by methods of the present invention.

In one non-limiting example, the mutated MTAN enzyme is the MTAN from *Helicobacter pylori* (Hp), in which the aspartic acid residue at position 198 is mutated to an asparagine residue (MTAN-D198N). When bound to MTAN-D198N, AdoHcy-TAMRA, as illustrated in FIG. 1A, demonstrates a $K_d$ value in the low nM range, which allows for a wide range of concentrations to be resolved while performing competitive FP assays. The results from competitive FP experiments described below highlight the versatility and sensitivity of measuring various generated products from AdoMet-dependent as well as ATP-dependent enzymes, including AdoHcy, MTA, ADP, and AMP (FIG. 1). Notably, the competitive fluorescence-based methods according to the present invention described herein provide an alternative to presently-known assays for monitoring the activity of MTases that are highly sensitive, cost effective, and suitable for high-throughput screening.

Accordingly, the displacement of the AdoHcy-TAMRA and other similar fluorescent probes from MTAN-D198N, or an analogous mutation to an MTAN enzyme within EC 3.2.2.9, as it is replaced within the active site by the adenosine-containing compound can be monitored using fluorescence-based methods, including fluorescence polarization. While presently-known fluorescently-tagged AdoHcy and AdoMet analogs have typically contained a fluorophore on the adenine or 5'-thio moieties (See Graves, above; see also Yi, J. S., et al., *ACS Chem. Biol.* 2015, 10, 667-674 and Brown, L. J., et al., *Anal. Biochem.* 2014, 467, 14-21), the active site cavity of HpMTAN is compact, and accommodation of a fluorophore conjugated to either of the aforementioned moieties would potentially disrupt essential interactions between the fluorescent probe and residues in the MTAN active site cavity.

Conversely, examination of the crystal structure for MTAN-D198N complexed with AdoHcy illustrates that the α-amino moiety of AdoHcy is not buried in the active site, but is positioned at the protein surface (FIG. 2) (See Mishra, V., et al., *ACS Biochem.* 2012, 51, 9763-9772). Without being limited by a particular theory, it is believed that placement of a fluorophore on the α-amino moiety of AdoHcy maintains essential interactions for the fluorescently-labeled ligand within the active site cavity and promotes high-affinity binding of the fluorescent probe. Those skilled in the art would appreciate that there are numerous other linking groups can extend from the 5'-carbon of the ribosyl moiety within adenosine to a covalently-linked fluorophore that is oriented outside of the binding pocket, and that AdoHcy represents merely one such example. As illustrated in FIG. 2, a linear chain of six or more atoms extending from the 5'-carbon is sufficient to extend outside of the binding pocket and enable the binding of a fluorescent probe.

Figure 4:
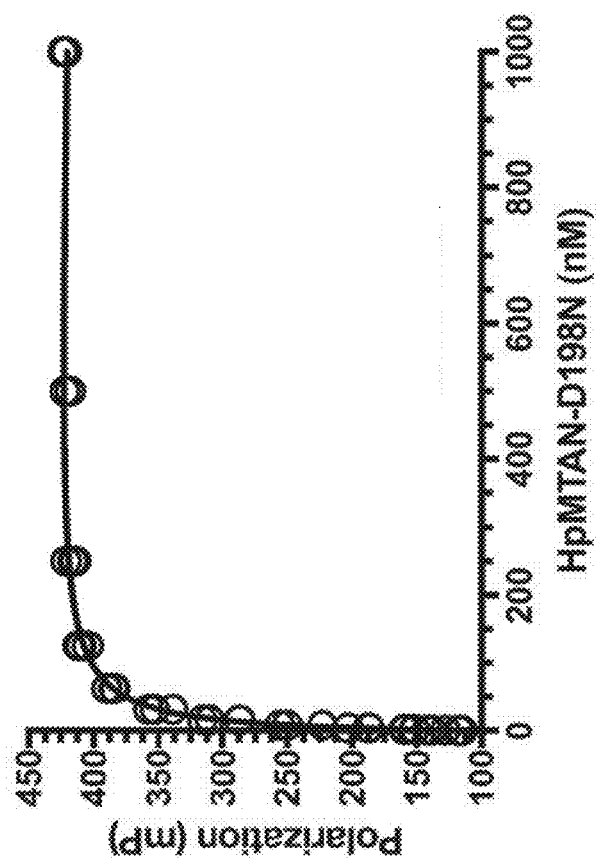
FIG. 4 shows a binding isotherm of AdoHcy-TAMRA coupled to the inactivated MTAN enzyme.

As a result, in another embodiment, the synthetic approach for making a fluorescent probe for use with methods and kits of the present invention involves a nucleophilic acyl substitution in a one-pot synthesis by combining AdoHcy with SE-TAMRA, which is a rhodamine derivative containing an amine-reactive moiety (FIG. 3), to form AdoHcy-TAMRA. In slightly basic conditions, the α-amino group of AdoHcy attacks the electrophilic center of the succinimidyl ester linkage of SE-TAMRA, resulting in the formation of an amide linkage between TAMRA and AdoHcy. Once the fluorescent probe is synthesized, the protein-probe complex can be formed by incubating MTAN-D198N with AdoHcy-TAMRA at ambient temperature for at least 10 minutes, including at least 15, 20, 25, or 30 minutes, up to at least 60 minutes. In other further embodiments AdoHcy and SE-TAMRA are incubated for less than 60 minutes, including less than 30, 25, 20, or 15 minutes, down to less than 10 minutes. Equilibrium binding studies between AdoHcy-TAMRA and MTAN-D198N are described below. The generated binding isotherm between AdoHcy-TAMRA and MTAN-D198N demonstrates that AdoHcy-TAMRA possesses high affinity to MTAN-D198N exhibiting a determined $K_d$ value of 11.3±0.7 nM (FIG. 4).

In contrast, other previously-characterized adenosine-containing compounds, MTA and AdoHcy, that have been characterized with HpMTAN have exhibited low p M affinity by measuring the spectral change of the reaction through formation of adenine (See Firestone, R. S., et al., *Anal. Chem.* 2016, 88, 11860-11867). Further, steady-state kinetic analysis using a luciferase-based assay for *Staphylococcus aureus* MTAN elicited negative cooperativity between the two monomers demonstrating $K_m$ values for MTA of 100 nM and 900 nM for the first and second active site, respectively.

Here, the binding isotherm of AdoHcy-TAMRA represents the affinity measured for the first active site binding event, which affords the high sensitivity of the developed FP assay. Fluorescent probes possessing high affinity for their target exhibit several benefits including being cost effective, reduced aggregation of fluorophores, and the capability of resolving a wide range of ligand affinities. Conventional wisdom within the art has previously indicated that competitive FP assays with tight-binding fluorescently-labeled ligands should be avoided when measuring the potency of inhibitors with intermediate affinity (See Huang, X. *J Biomol. Screen* 2003, 8, 34-38). However, tight-binding fluorescently labeled ligands provide an extended range of inhibitor potency in comparison to moderate affinity fluorescently-labeled ligands.

Furthermore, determination and assessment of a Z'-factor also indicates that the FP adenosine quantification assay is reproducible. Z' is a statistical measure that evaluates the quality of an assay, where calculated values greater than 0.5 demonstrate a suitable assay (See Zhang, J., et al., *J. Biomol. Screening* 1999, 4, 67-73). Typically, the concentration of assay components used in the assessment of the Z'-factor should mirror the concentrations to be used under the conditions of the competitive assay. In another embodiment of the present invention, the concentration of AdoHcy-TAMRA fluorescent probe used in competitive FP assays can equal the calculated $K_d$ value, 11.3 nM. In other embodiments of the invention, MTAN-D198N can be included at a concentration in which about 70 to about 80 percent of the MTAN-D198N forms a complex with the probe. In further embodiments, the MTAN-D198N concentration is 50 nM.

Under assay conditions in which the AdoHcy-TAMRA was 11.3 nM and the MTAN-D198N is 50 nM (see the examples below), the determined Z'-factor for the FP assay is 0.77, illustrating the FP assay's suitability to quantify adenosine-containing compounds in a solution.

In some embodiments of the invention, methods of the present invention that utilize competitive fluorescence polarization and fluorescence resonance energy transfer (FRET, further described below) can be utilized to quantify adenosine-containing compounds that are produced as a result of the catalytic activity of AdoMet-dependent enzymes, particularly MTases. In further embodiments, the adenosine-containing compound is selected from the group consisting of AdoHcy, MTA, ATP, ADP, and AMP. In even further embodiments, the adenosine-containing compound is AdoHcy.

Adapting the MTAN-D198N/AdoHcy-TAMRA protein-probe complex for quantifying adenosine-containing compounds, particularly AdoHcy or MTA, generated from AdoMet-dependent enzymes is contingent on the sensitivity and capability of differentiating the adenosine-based products from substrates. For instance, assays that monitor MTase activity require high sensitivity due to inherently slow catalytic turnover or avoiding product inhibition at high concentrations of AdoHcy (See Hendricks, above; and Luo, above; see also Cannon, L. M., et al., *Anal. Biochem.* 2002, 308, 358-363).

In another embodiment, the protein-probe complex can be utilized within a competitive FP assay to directly detect adenosine-containing compounds by monitoring the displacement of the fluorescent probe from MTAN-D198N or an analogously mutated MTAN enzyme. Without being limited by a particular theory, it is believed that the adenosine-containing compound competes with the fluorescent probe for the binding site within mutated MTAN, displacing the probe and causing a change in the rotational motion of the probe, since it is no longer bound to the enzyme. As the concentration of the adenosine-compound increases, the rotation of the probe also increases and causes a decrease in the polarization of the sample.

Figure 5:
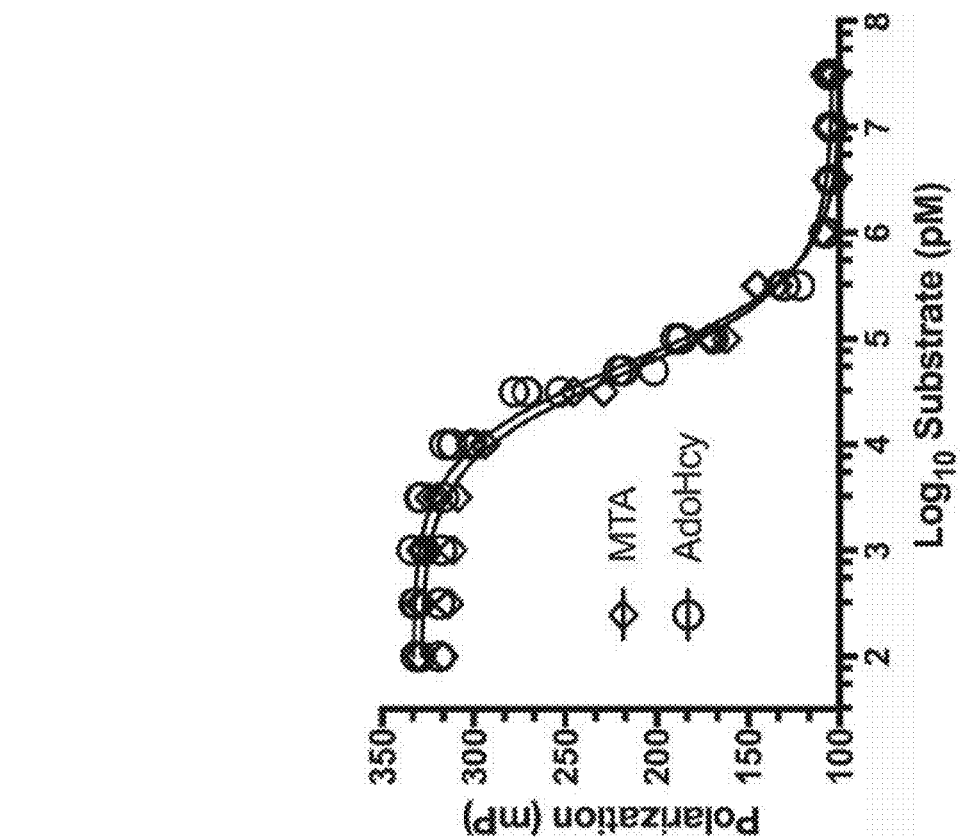
FIG. 5 shows displacement curves of MTA and AdoHcy with inactivated MTAN and AdoHcy-TAMRA.

Similarly, the limit of detection (LOD) of the competitive FP assay is unique for each adenosine-containing compound, based in part on the affinity of the adenosine-containing compound for the binding site of the MTAN-D198N enzyme. It has been observed that the LOD for the competitive FP assay is 10 nM for MTA and 6 nM for AdoHcy. Accordingly, calculated $K_i$ values for MTA and AdoHcy from data collected using the competitive FP assay (see Example 5, below) are also in the low nM range, at 24.2±1.2 and 29.5±3.6 nM, respectively. Displacement curves for MTA and AdoHcy are shown in FIG. 5.

In other embodiments, the present invention provides methods for assessing the kinetic parameters of AdoMet- or ATP-dependent enzymes that form adenosine-containing compounds as products. In further embodiments, the AdoMet-dependent enzyme is an MTase. In other further embodiments, the adenosine-containing compound formed by the activity of the MTase is AdoHcy. The LOD of AdoHcy using methods of the present invention is notably better or at least comparable to other previously published spectroscopic, fluorescence-based or FP immunoassays for measuring MTase activity (see Ibanez, above; Dorgan, above; and Graves, above; see also Klink, T. A., et al., *J. Biomol. Screen.* 2012, 17, 59-70). Several developed assays for MTases require multiple coupled enzymes to manipulate generated products into producing an output signal, which can lower the sensitivity of the assay. In contrast, coupling the MTAN-D198N/AdoHcy-TAMRA complex directly to AdoMet-dependent enzymes provides a highly sensitive universal assay that immediately detects generated products without the complication of additional auxiliary enzymes.

Figure 6B:
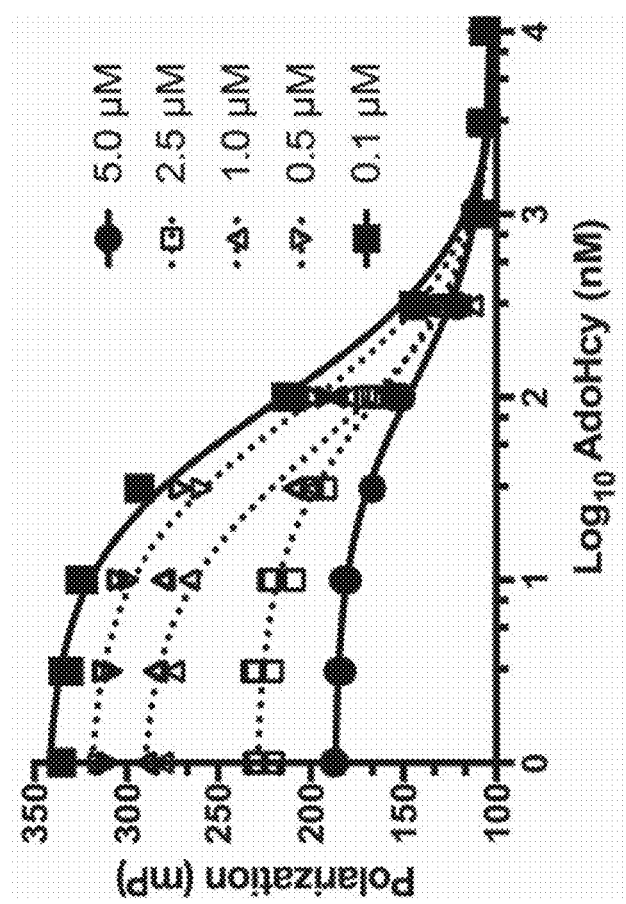
FIG. 6B shows displacement curves of AdoHcy in the presence of varying concentrations of AdoMet.
Figure 6A:
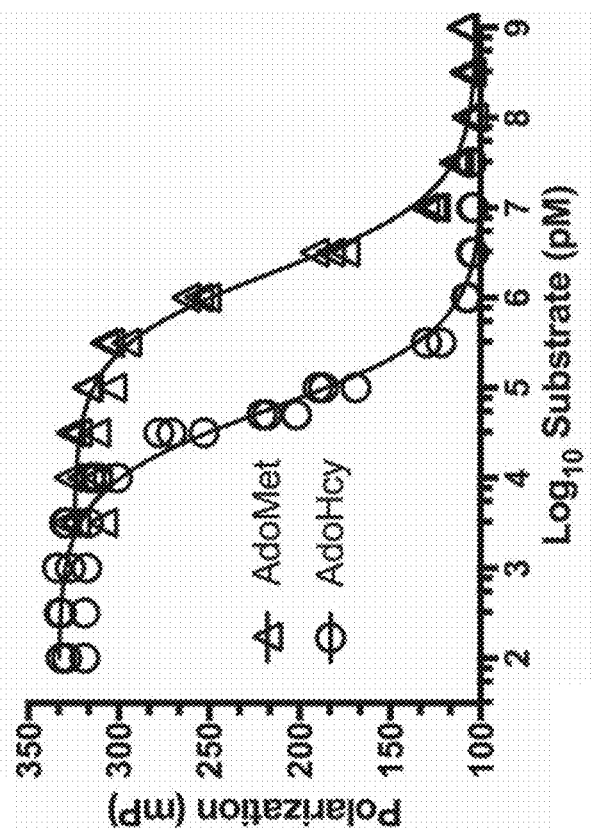
FIG. 6A shows displacement curves of AdoMet and AdoHcy with inactivated MTAN and AdoHcy-TAMRA.

Typically, kinetic characterization of AdoMet-dependent enzymes typically requires relatively high concentrations of AdoMet, potentially interfering with the HpMTAN-D198N/AdoHcy-TAMRA competitive FP assay. As illustrated in FIG. 6A, although the $K_i$ of AdoMet is considerably weaker than AdoHcy (989±160 nM compared to 29.5±3.6 nM, respectively) the change in fluorescence polarization as a result of the presence of AdoMet within the system is non-negligible. Even though the calculated LOD of AdoMet is 312 nM, which is much higher than that of the AdoHcy, the presence of the AdoMet nonetheless increases the LOD of AdoHcy, as illustrated in FIG. 6B. As a result, it has been observed that the concentration of AdoMet must be less than about 5 µM in order to be able to reliably detect the presence of adenosine-containing molecules in the same solution. However, despite the background interference caused by AdoMet at higher concentrations, the developed competitive FP assay clearly discriminates between adenosine-containing compounds, particularly AdoHcy and MTA, and AdoMet, resulting in a dynamic range that affords accurate measurement of AdoHcy/MTA production in a workable background of AdoMet.

Figure 7A:
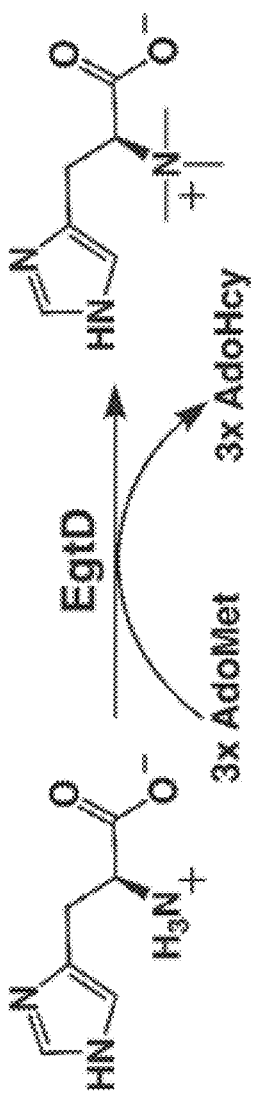
FIG. 7A shows the general reaction scheme for the EgtD enzyme.

In another embodiment, methods of the present invention can be utilized to assess the kinetic parameters of AdoMet-dependent MTases in which the AdoMet concentration within the reaction mixture is less than 5 µM. In one non-limiting example, the kinetic parameters of L-histidine methylation by an AdoMet-dependent MTase enzyme, EgtD, encoded by *Mycobacterium tuberculosis*, can be examined and characterized using non-saturating steady state kinetics. EgtD catalyzes the initial step in the biosynthesis of ergothioneine by catalyzing the trimethylation of the α-amino acid moiety of L-histidine (FIG. 7A) (See Jeong, J. H., et al., *Biochem. Biophys. Res. Commun.* 2014, 452, 1098-1103, and Vit, A., et al., *Chem. Biochem.* 2015, 16, 119-125). Similar to MTAN-D198N, EgtD can be expressed and purified by any means known in the art, including as described below in Example 7.

Figure 7B:
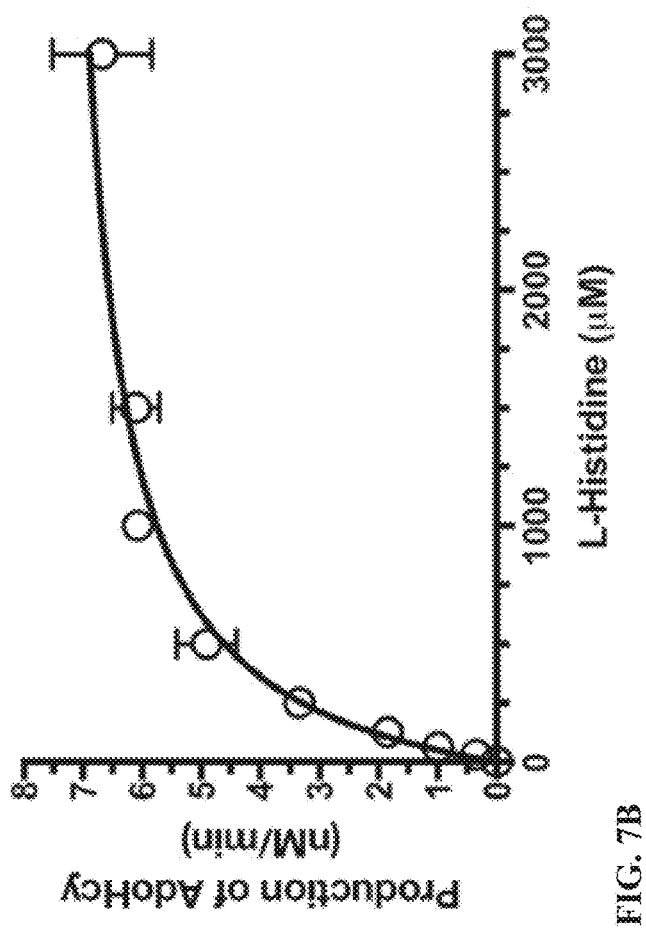
FIG. 7B shows a Michelis-Menten curve for L-histidine to EgtD using the HpMTAN-D198N/AdoHcy-TAMRA competitive FP assay.

Previously, determination of the affinity for L-histidine and AdoMet to *Mycobacterium smegmatis* EgtD using isothermal calorimetry showed $K_d$ values of 290±14 and 270±20 µM, respectively. In contrast, kinetic characterization of L-histidine by EgtD at non-saturating AdoMet concentrations using the developed competitive FP assay demonstrated a $K_m^{app}$ value of 330±35 µM (FIG. 7B), which is within error of the previously determined $K_d$ value for the homolog (see Example 8, below). Although pseudo-first order kinetics could not be performed because of the interference of background AdoMet at higher concentrations, experiments to determine steady-state kinetic parameters could be conducted to approximate the $K_m$ value for substrates using the developed competitive FP assay.

Figure 8:
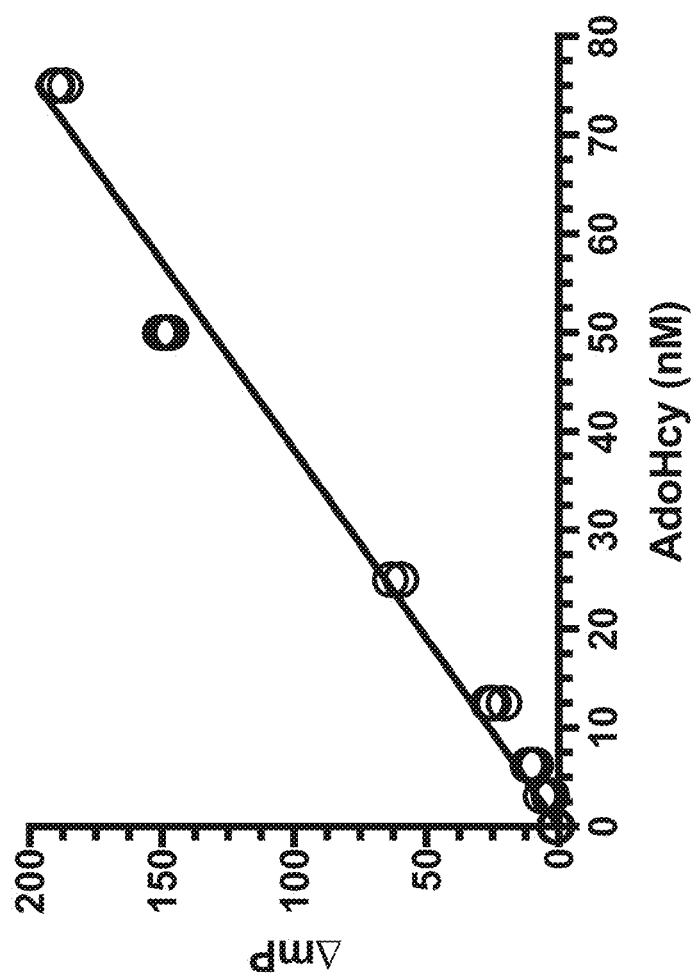
FIG. 8 shows a standard curve of the change in polarization as a function of AdoHcy concentration in the presence of 500 nM AdoMet.

In order to determine the rate of production of AdoHcy by EgtD and calculate the apparent $K_m$ value, a standard curve must be generated to indicate the change in the polarization from the maximum, $MP_{max}$ as a function of the increasing AdoHcy concentration (FIG. 8). Because of the negative effect of AdoMet on the assay's ability to detect the presence of AdoHcy, the standard curve must be generated in the presence of the same concentration of AdoMet that is used in the EgtD reaction. As illustrated in Example 8 and FIG. 8, the concentration of AdoMet used to study EgtD was 500 nM.

In another embodiment, the interference in fluorescence polarization as a result of the presence of AdoMet within the aqueous composition can be reduced or eliminated by modifying other amino acid residues within the mutated MTAN enzyme that are associated with coordinating AdoMet and/or AdoHcy in the binding site. As illustrated by the crystal structure of MTAN-D198N in the presence of AdoHcy illustrated in FIG. 9, there are several residues that undergo van der Waals interactions (indicated by dashed lines, with distances shown in Å) with the thioether moiety, including 152, L104, F153, and M174. The sulfur atom of AdoHcy forms van der Waals interactions at distances ranging from 3.8 to 4.2 Å with 152, L104, F153, and M174. Each of these residues are 100% conserved in bacterial MTAN orthologs with the exception of L104. However, the analogous residue in bacterial MTAN orthologs is one of the following aliphatic residues: alanine, valine, isoleucine, or leucine.

Figure 9:
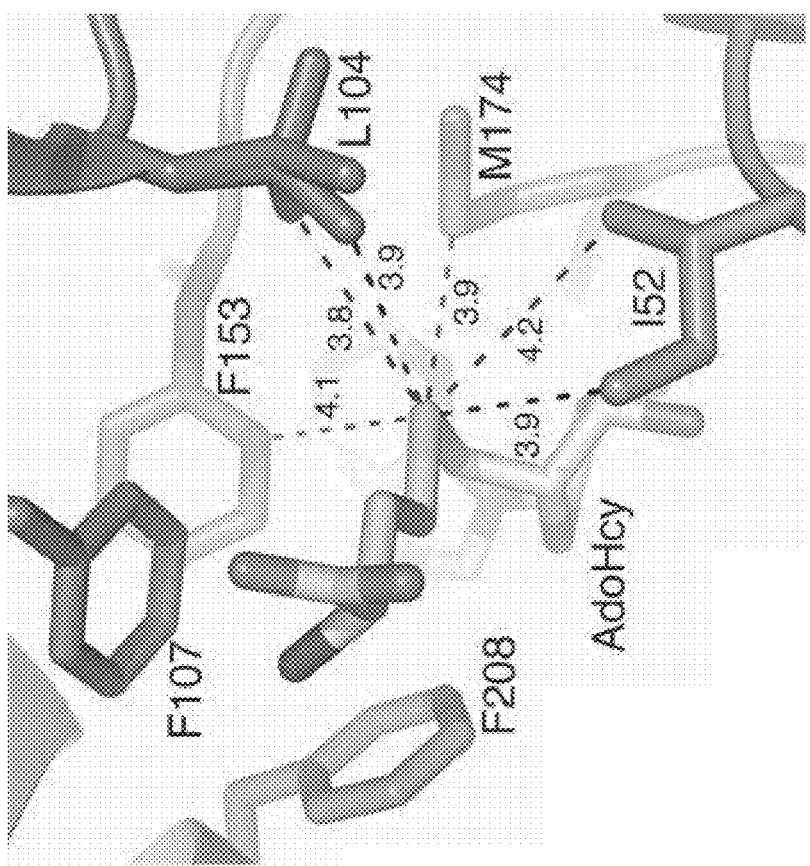
FIG. 9 shows a view of the inactivated binding site within HpMTAN-D198N, illustrating amino acid residues involved in coordinating with the thioether moiety of AdoHcy.

Without being limited by a particular theory, variation of residue L104 offers the best opportunity because multiple conformations are observed for the L104 side chain in the X-ray crystal structure (FIG. 9). A mutation to a methionine at this position maintains the hydrophobic nature of the side chain but would slightly increase the accessible surface area of the side chain from 137 Å$^2$ for leucine to 160 Å$^2$ for methionine.

In addition to mutating L104, mutations at other thioether-interacting residues can be made in an effort to negatively affect AdoMet binding affinity, particularly at residues 152, F153, and M174, by imparting added steric bulk or a positive charge to cause charge repulsion between MTAN and the methyl sulfonium moiety of AdoMet. In particular, I52M and L104M variants can be made to increase steric bulk and maintain hydrophobicity, while I52R, L104R, F153R and M174R variants can be made to incorporate a positively-charged residue.

Thus, in another embodiment, at least one mutation can be engineered into at least one of four positions within SEQ ID NO: 1, Ile-52, Leu-104, Phe-153, and Met-174, which correspond to the residues 152, L104, F153, and M174 within FIG. 9. Mutated MTAN enzymes with at least one mutation at one of these positions comprise the amino acid sequence of SEQ ID NO: 8, which contains residues having the designation, "Xaa," illustrating known instances in which the amino acid at that position can be selected from a group of two or more amino acids.

In another embodiment, at least one of the natural amino acid residues at position 52, position 104, position 153, and position 174 can be mutated to any other amino acid residue through random mutagenesis. In other embodiments, at least one of the natural amino acid residues at position 52, position 104, position 153, and position 174 can be conservatively mutated to either a sterically bulky amino acid residue, including but not limited to methionine, or a positively-charged residue, including but not limited to arginine. In further embodiments, within mutated MTAN enzymes comprising the amino acid sequence of SEQ ID NO: 8, the residue at X52 is either isoleucine, methionine, or arginine. In other further embodiments, within mutated MTAN enzymes comprising the amino acid sequence of SEQ ID NO: 8, the residue at X104 is either leucine, methionine, or arginine. In still other further embodiments, within mutated MTAN enzymes comprising the amino acid sequence of SEQ ID NO: 8, the residue at X153 is phenylalanine or arginine. In yet still other further embodiments, within mutated MTAN enzymes comprising the amino acid sequence of SEQ ID NO: 8, the residue at X174 is methionine or arginine.

In another non-limiting example in which the protein-probe complex is utilized in accordance with methods of the present invention, the kinetic parameters of ATP hydrolysis by ATP-dependent calf intestinal alkaline phosphatase (CIAP) to produce ADP, AMP, and adenosine were also determined using the competitive FP assay according to methods of the present invention. Previously, Michelis-Menten kinetics performed on CIAP using a molybdenum blue-based assay exhibited substrate inhibition of ATP at low µM concentrations, which resulted in a $K_m$ value of 20.5 µM and a $K_i$ value of 19.0 µM (FIG. 10A) (see Fernley, H. N., et al., *Biochem. J.* 1967). Steady-state analysis of CIAP using the developed competitive FP assay demonstrates a $K_m$ value of 0.9±0.2 µM and $K_i$ value of 7.6±1.8 µM for substrate inhibition of ATP. Without being limited by theory, it is believed that decreased $K_m$ and $K_i$ values measured for ATP using the competitive FP assay are likely a result of the increased sensitivity, stemming from not requiring an equivalent concentration of magnesium chloride that is needed in the molybdenum blue-based assay. However, while the observed results exhibit an overall increase in adenosine-containing compounds, the assay cannot distinguish between ADP, AMP, or adenosine.

Figure 10B:
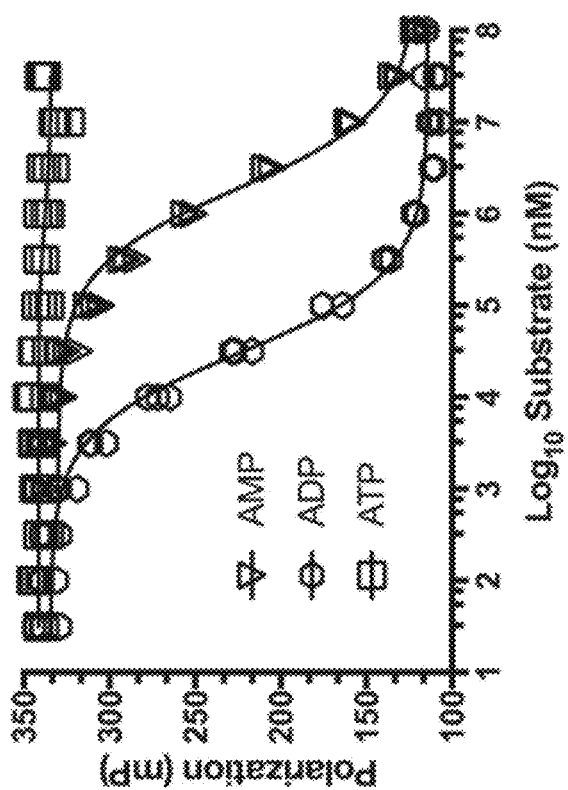
FIG. 10B shows displacement curves of ATP, ADP, and AMP using the HpMTAN-D198N/AdoHcy-TAMRA competitive FP assay.
Figure 10A:
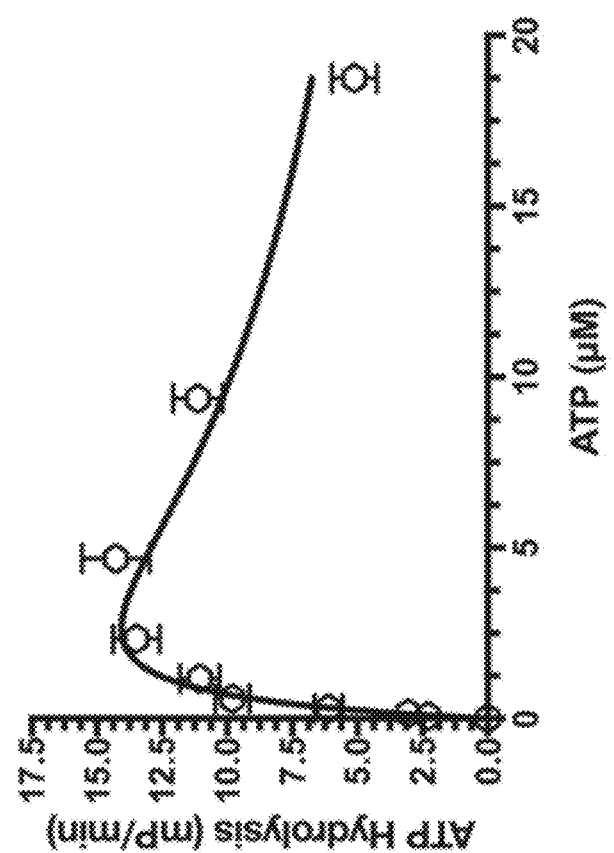
FIG. 10A shows a Michelis-Menten curve of alkaline phosphatase exhibiting substrate inhibition in response to the presence of ATP.

Nonetheless, while ADP, AMP, and adenosine are all indistinguishable in the context of the CIAP reaction, they do bind differentially with MTAN-D198N, as illustrated in FIG. 10B. ADP and AMP both show M affinity to MTAN-D198N, whereas ATP is unable to displace AdoHcy-TAMRA from the enzyme. Consequently, the capability of differentiating AMP and ADP from ATP suggests that the developed competitive FP methods of the present invention represent an alternative assay for measuring the activity of ATP-dependent enzymes. Currently, several assays exist commercially to monitor the activity of kinases (see Ishida, A., et al., *J. Pharmacol. Sci.* 2007, 103, 5-11). Most of these assays do not tolerate a high background concentration of ATP (see Li, H., et al., *Assay Drug Dev. Technol.* 2009, 7, 598-605), whereas the developed competitive FP assay tolerates up to 100 mM ATP, which is more than one order of magnitude higher ATP concentration to be tolerated in comparison to standard kinase assays. The advantage of tolerating a wide range of ATP concentrations is that the assay can easily determine and accommodate a diverse range of $K_m$ values for ATP exhibited by kinases as well as allow for ATP competitiveness studies.

In another embodiment, methods according to the present invention for quantifying adenosine-containing compounds within an aqueous composition utilize a FRET assay, in which fluorescence by the fluorescent probe within an MTAN protein-probe complex in the presence of a covalently cross-linked secondary fluorophore is compared against the fluorescence of the unbound fluorescent probe. Similar to FP assay methods of the present invention, the quantity of adenosine-containing compounds can be quantified using FRET methods of the present invention in real time during chemical reactions in which adenosine-containing compounds are generated as a product. In further embodiments, methods for quantifying adenosine-containing compounds in an aqueous composition using FRET comprise the steps of: (a) providing a fluorescent probe comprising an adenosine scaffold comprising an adenine moiety and a ribosyl moiety, and a TAMRA fluorophore, wherein the adenosine scaffold is covalently bound to the fluorophore by a linking portion comprising a linear chain of six or more atoms extending from the 5'-carbon of the ribosyl moiety to the 5-carboxyl functional group within TAMRA; (b) providing a mutated MTAN enzyme, wherein the mutated MTAN enzyme comprises an amino acid sequence selected from the group consisting of SEQ ID NO: 4, SEQ ID NO: 6, and SEQ ID NO: 8, and a cysteine residue that is conjugated to a secondary fluorophore comprising a fluorescently-active moiety and a thiol-reactive crosslinker that bridges the fluorescently-active moiety to the cysteine residue; (c) forming a protein-probe complex between the mutated MTAN enzyme and the fluorescent probe; (d) measuring the fluorescence intensity of the fluorescent probe within the protein-probe complex; (e) combining an adenosine-containing compound with the protein-probe complex to form an adenosine quantification mixture; (f) measuring the increase of fluorescence intensity of the fluorescent probe in the presence of the adenosine quantification mixture; and calculating the amount of the adenosine-containing compound within the adenosine quantification mixture using the increase of fluorescence intensity of the fluorescent probe in the presence of the adenosine quantification mixture.

Without being limited by a particular theory, it is believed that FRET can reduce or eliminate elevated false-positive rates that are observed in some FP-based assays, particularly in reaction conditions that demonstrate a high amount of autofluorescence of other compounds that are present within an aqueous composition or reaction mixture. FRET-based assays according to the present invention are similarly suited to utilize any of the fluorescent probes discussed above, particularly AdoHcy-TAMRA, in association with a secondary fluorophore that is covalently linked to a different portion of the same mutated MTAN molecule.

Typically, secondary fluorophores that are covalently linked to a polypeptide are conjugated to a cysteine residue located on the periphery of the polypeptide. However, cysteine residues are typically found in internal portions of enzymes as part of an S—S disulfide bridge formed with a second cysteine residue. As a result, one or more cysteine residues must be engineered into the mutated MTAN sequence. Thus, in another embodiment, the sequence of the HpMTAN-D198N enzyme can further comprise a mutation to a cysteine residue at one or more positions on the periphery of the enzyme that are within less than about 20 Å from the α-amino group of the AdoHcy moiety when the fluorescent probe is bound within the active site, including less than about 18, 16, 14, 12, 10, or 8 Å, down to less than about 6 Å from the α-amino group of the AdoHcy moiety when the fluorescent probe is bound within the active site. In other embodiments, the amino acid sequence of the MTAN-D198N enzyme can further comprise a mutation to a cysteine residue at one or more positions on the periphery of the enzyme that are within at least 6 Å from the α-amino group of the AdoHcy moiety when the fluorescent probe is bound within the active site, including at least about 8, 10, 12, 14, 16, or 18 Å, up to at least about 20 Å from the α-amino group of the AdoHcy moiety when the fluorescent probe is bound within the active site.

Figure 11:
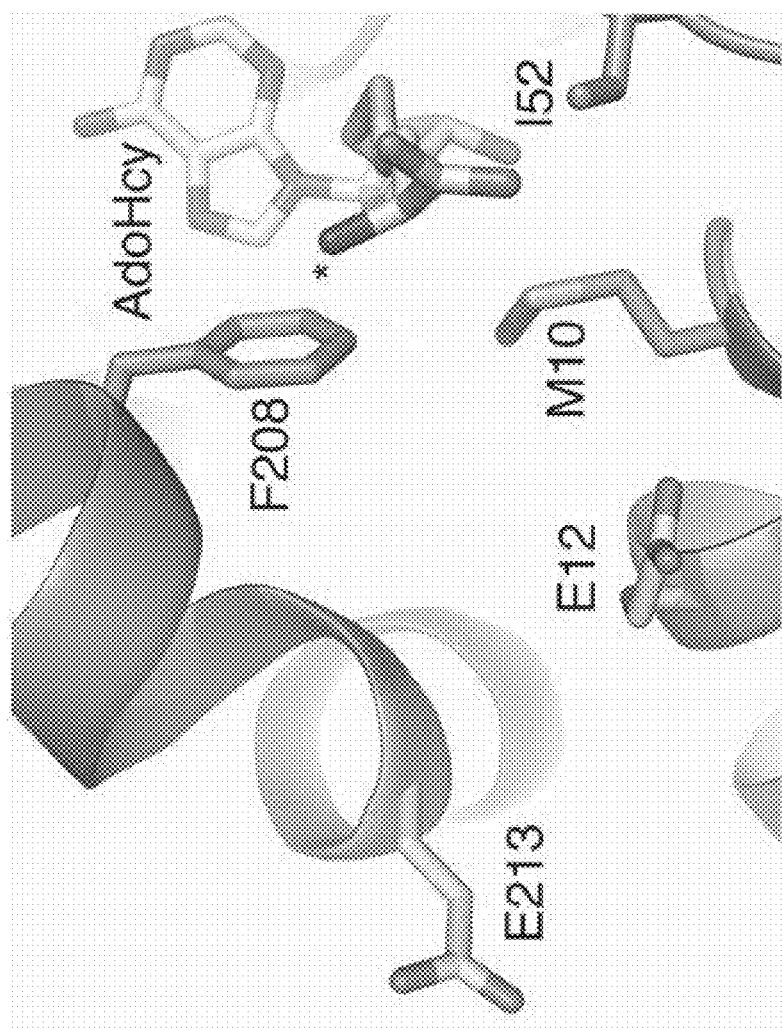
FIG. 11 shows a view of amino acid residues near the MTAN AdoHcy-binding site which can be mutated to a cysteine residue and cross-linked to a secondary fluorophore in accordance with FRET-based quantification methods of the present invention.

Within SEQ ID NO: 1, there are two glutamic acid residues located on the periphery of the polypeptide that are within 15 Å of the inactivated binding site, Glu-12 and Glu-213 (8 Å and 14 Å, respectively) and can be mutated to a cysteine residue, as illustrated in FIG. 11. Within FIG. 11, the asterisk on the AdoHcy indicates the TAMRA attachment site for the fluorescent probe. In some further embodiments, the mutated MTAN enzyme further comprises a glutamic acid to cysteine mutation at position 12. In even further embodiments, the mutated MTAN enzyme comprises the amino acid sequence of SEQ ID NO: 4. In other further embodiments, the mutated MTAN enzyme further comprises a glutamic acid to cysteine mutation at position 213. In even further embodiments, the mutated MTAN enzyme comprises the amino acid sequence of SEQ ID NO: 6. In still other further embodiments, a mutated MTAN enzyme comprising the amino acid sequence of SEQ ID NO: 8 can contain a glutamic acid to cysteine mutation at either or both of position 12 or position 213.

Within mutated MTAN enzymes that further comprise one or more peripheral mutations to a cysteine residue, the cysteine residue can then be further conjugated to a secondary fluorophore comprising a fluorescently-active moiety and a thiol-reactive crosslinker that bridges the fluorescently-active moiety to the cysteine residue. In some embodiments, within enzymes comprising the amino acid sequence of SEQ ID NO: 4, Cys-12 is conjugated to the secondary fluorophore. In further embodiments, the amino acid at position 12 within SEQ ID NO: 8 is selected to be a cysteine residue, and Cys-12 is conjugated to the secondary fluorophore. In other embodiments, within enzymes comprising the amino acid sequence of SEQ ID NO: 6, Cys-213 is conjugated to the secondary fluorophore. In further embodiments, the amino acid at position 213 within SEQ ID NO: 8 is selected to be a cysteine residue, and Cys-213 is conjugated to the secondary fluorophore.

In typical fluorescence-based assays, a fluorophore absorbs light at its maximum absorption wavelength ($\lambda_{max,abs}$), and the emission of fluorescence is monitored at a longer wavelength that is typically the fluorophore's maximum emission wavelength ($\lambda_{max,em}$). Typical fluorophores include conjugated, organic dyes, fluorescent proteins, and quantum dots. In a typical FRET-based assay, the $\lambda_{max,abs}$ of the secondary fluorophore overlaps with the with the $\lambda_{max,em}$ of the primary fluorophore. Thus, in some embodiments, FRET-based methods of the present invention that utilize TAMRA within the fluorescent probe are paired with a secondary fluorophore with a $\lambda_{max,abs}$ that overlaps with the $\lambda_{max,em}$ of TAMRA. Example secondary fluorophores include, but are not limited to DABCYL-maleimide and QSY™ 7 $C_5$-Maleimide.

In another embodiment, the thiol-reactive crosslinker that conjugates the secondary fluorophore to Cys-12 or Cys-213 can comprise any thiol-reactive functional group. Thiol-reactive functional groups that are typically utilized in conjunction with fluorescent labeling of biomolecules include haloacetyl, maleimide, or vinyl amide groups. In further embodiments, the thiol-reactive crosslinker comprises a maleimide group. Additionally, compounds that are acceptors in Michael addition reactions can also be utilized. One non-limiting example of a Michael acceptor that interacts with a fluorophore as a Michael donor is benzylideneacetone.

In general, the mutated MTAN enzymes encoded by the disclosed amino acid sequences, particularly enzymes comprising the amino acid sequence of SEQ ID NO: 1, SEQ ID NO: 4, SEQ ID NO: 6, and SEQ ID NO: 8, can be expressed and purified using any microbiological technique known in the art, including as described below. The engineered gene products, proteins and polypeptides of the present invention can also include analogs that contain insertions, deletions, or mutations relative to the disclosed DNA or peptide sequences, and that also encode for mutated MTAN enzymes comprising a D198N or analogous mutation within the active site to inactivate the enzyme. Those skilled in the art will appreciate that other analogs, as yet undisclosed or undiscovered, can be used to design and/or construct analogs of a particular mutated MTAN enzyme of the present invention. Further, the gene products, proteins, and polypeptides discussed and disclosed below can also include fusion or recombinant mutated MTAN enzymes comprising full-length sequences or segments of sequences disclosed in the present invention. Methods of preparing such proteins are known in the art.

In another embodiment, aqueous compositions utilized during expression, purification, or storage of mutated MTAN enzymes, particularly SEQ ID NO: 4, SEQ ID NO: 6, and SEQ ID NO: 8 can comprise a reducing agent, for example dithiothreitol or tris(2-carboxyethyl)phosphine (TCEP), in order to reduce or eliminate unwanted disulfide bond formation between cysteine residues on one or more mutated MTAN molecules. In even further embodiments, the reducing agent is TCEP.

In addition to the nucleic acid and amino acid sequences disclosed herein, the present invention also includes any such sequences that are substantially identical to a nucleic acid sequence (SEQ ID NO: 2, SEQ ID NO: 5, and SEQ ID NO: 7) or amino acid (SEQ ID NO: 1, SEQ ID NO: 4, SEQ ID NO: 6, and SEQ ID NO: 8) sequence disclosed herein. "Substantially identical" sequences, as used in the art, refer to sequences which differ from a particular reference sequence by one or more deletions, substitutions, or additions, the net effect of which is to retain at least some of the ability of the mutated MTAN enzyme to bind to adenosine-containing compounds, including the fluorescent probe.

Additionally, alternate nucleic acid sequences that include functionally equivalent codons are also encompassed by this invention. Functionally equivalent codons refer to codons that encode the same amino acid, such as the ACG and AGU codons for serine. Thus, substitution of functionally equivalent codons into the sequence examples of SEQ ID NO: 2, SEQ ID NO: 5, or SEQ ID NO: 7 ultimately encode for equivalent mutated MTAN enzymes that bind to adenosine-containing compounds, including the fluorescent probe.

In another embodiment, isolated nucleic acids, or functional fragments thereof, that encode for the mutated MTAN enzymes of the present invention are provided. In particular embodiments, the mutated MTAN enzymes comprise an amino acid sequence selected from the group consisting of SEQ ID NO: 1, SEQ ID NO: 4, SEQ ID NO: 6, and SEQ ID NO: 8. In other embodiments, the present invention provides isolated nucleic acids encoding functional fragments of the mutated MTAN enzymes of the present invention, or variants thereof in which conservative substitutions have been made for particular residues within SEQ ID NO: 1, SEQ ID NO: 4, SEQ ID NO: 6, or SEQ ID NO: 8.

The isolated nucleic acids of the present invention may be joined to other nucleic acid sequences for use in various applications. Thus, for example, the isolated nucleic acids may be ligated into cloning or expression vectors, as are commonly known in the art and as described in the examples below. Furthermore, nucleic acid segments of the present invention, regardless of the length of the coding sequence itself, can be combined with other DNA sequences, for example promoters, enhancers, polyadenylation signals, additional restriction enzyme sites, multiple cloning sites, and other coding segments, such that their overall length can vary considerably. Those skilled in the art would recognize that a nucleic acid fragment of almost any length can be employed, with the total length typically being limited by the ease of preparation and use in the intended recombinant DNA protocol.

In particular, recombinant vectors in which the coding portion of the gene or DNA segment is positioned under the control of a promoter are especially useful. In some embodiments, the coding DNA segment can be associated with promoters isolated from bacterial, viral, eukaryotic, or mammalian cells. Promoters specific to the cell type chosen for expression are often the most effective. The use of promoter and cell type combinations for protein expression is generally known to those of skill in the art of molecular biology (See, e.g., Sambrook et al. (2012) *Molecular Cloning: A Laboratory Manual*, Fourth Edition, Cold Spring Harbor Laboratory Press, Cold Spring Harbor, N.Y., incorporated by reference in its entirety). The promoters employed can be constitutive or inducible and can be used under the appropriate conditions to direct high-level expression of the introduced DNA segment, such as is advantageous in the large-scale production of recombinant proteins or peptides. Appropriate promoter systems that are often effective for high-level expression include, but are not limited to, the vaccinia virus promoter, the baculovirus promoter, and the Ptac promoter.

Thus, in some embodiments, the present invention provides an expression vector comprising a polynucleotide that comprises any nucleic acid sequence that encodes for a mutated MTAN enzyme of the present invention, particularly enzymes comprising the amino acid sequence of SEQ ID NO: 1, SEQ ID NO: 4, SEQ ID NO: 6, or SEQ ID NO: 8. In further embodiments, an expression vector comprises a polynucleotide comprising the nucleotide sequence of SEQ ID NO: 2, SEQ ID NO: 5, or SEQ ID NO: 7. In even further embodiments, any nucleic acid sequence encoding for an engineered enzyme of the present invention can be codon-optimized based on the expression host used to produce the enzyme. The preparation of recombinant vectors and codon optimization are well known to those of skill in the art and described in many references, such as, for example, Sambrook et al. (2012) *Molecular Cloning: A Laboratory Manual*, Fourth Edition, Cold Spring Harbor Laboratory Press, Cold Spring Harbor, N.Y.

The present invention also provides for cells or cell lines, both prokaryotic and eukaryotic, into which have been introduced the nucleic acids of the present invention so as to cause clonal propagation of those nucleic acids and/or expression of the proteins or peptides encoded thereby. Such cells or cell lines have utility in the propagation and production of the nucleic acids of the invention, as well as the production of the proteins of the present invention. As used herein, the term "transformed cell" is intended to embrace any cell, or the descendant of any cell, into which has been introduced any of the nucleic acids of the invention, whether by transformation, transfection, transduction, infection, or other means. Methods of producing appropriate vectors, transforming cells with those vectors, and identifying transformants are well known in the art (See, e.g., Sambrook et al. (2012) *Molecular Cloning: A Laboratory Manual*, Fourth Edition, Cold Spring Harbor Laboratory Press, Cold Spring Harbor, N.Y.). Prokaryotic cells useful for producing the transformed cells of the invention include members of the bacterial genera *Escherichia* (e.g., *E. coli*), *Pseudomonas* (e.g., *P. aeruginosa*), and *Bacillus* (e.g., *B. subtilis, B. stearothermophilus*), as well as many others well known and frequently used in the art. In some embodiments, an expression vector comprising a nucleotide sequence encoding for any mutated MTAN enzyme of the present invention, including nucleotides comprising the nucleic acid sequence of SEQ ID NO: 2, SEQ ID NO: 5, and SEQ ID NO: 7, can be comprised within an isolated host cell selected from the group consisting of a bacterial cell, a yeast cell, an insect cell, and a mammalian cell. In further embodiments, the host cell is *Escherichia coli*.

In another embodiment, competitive FP and FRET-based assay can be utilized to screen small molecules to determine whether they inhibit AdoMet- or ATP-dependent enzymes. In some embodiments, the AdoMet-dependent enzyme is an MTase. In other embodiments, the ATP-dependent enzyme is a kinase. Without being limited by theory, it is believed that small-molecule inhibition of AdoMet- or ATP-dependent enzymes can be observed when the small molecule disrupts the activity of the enzyme and either reduces or eliminates the ability of the enzyme to produce the adenosine-containing compound. Those skilled in the art would appreciate that the threshold for a "hit," i.e. a reduction of enzymatic activity below a certain value relative to a reaction without an inhibitor present, can be determined by the user, and can vary from user to user. However, it is common that the threshold for a hit is 3 standard deviations from the average value of the entire set of the screening data.

Notably, the design of the developed competitive FP or FRET-based assay provides an advantage when performing high-throughput screening by easily identifying and reducing the hit rate of interfering compounds with the assay. As stated previously, several current available methods for MTases require multiple coupling enzymes, which complicates high-throughput screening by increasing the number of false positives. The developed competitive FP or FRET-based assay simplifies high-throughput screening for MTases by only requiring the MTAN-D198N/AdoHcy-TAMRA complex, and easily identifying compounds interfering with the assay by observing an initial decrease in the signal window.

Furthermore, the AdoHcy-TAMRA ligand itself is advantageous for small-molecule inhibitor-screening applications as compared to other rhodamine-derived fluorophores, for example the commercially available Alexafluor® 488, that have an absorption maximum (495 nm), that is similar to several drugs, particularly anthracycline drugs such as epirubicin and idarubicin. Utilizing a fluorescent probe with absorption and emission properties similar to small molecule target compounds can increase interference and cause false positives. In contrast, TAMRA absorbs at a much longer wavelength (545 nm) that is more amenable to inhibitor-screening FP applications.

Figure 12B:
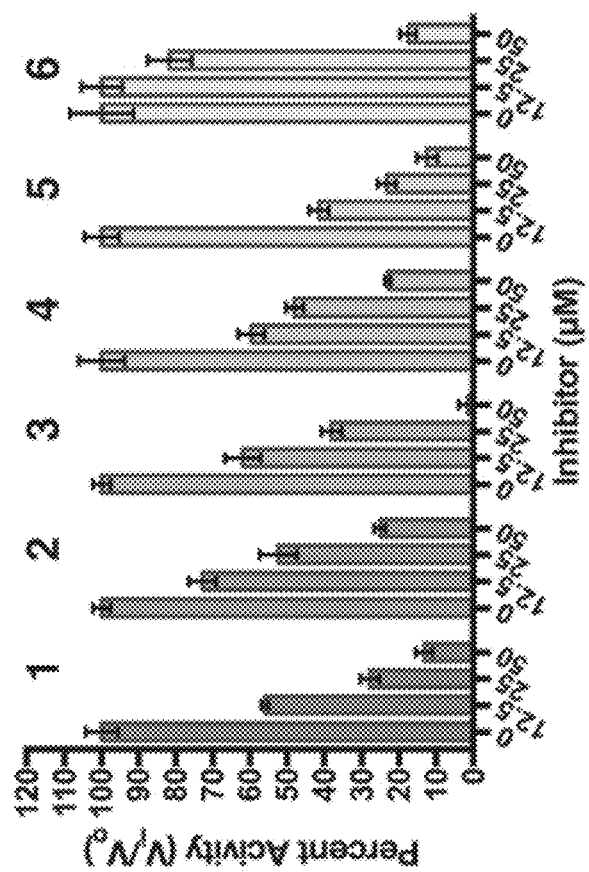
FIG. 12B shows the dose-dependent percent activity of EgtD with six confirmed hits from the NIH clinical collection.
Figure 12A:
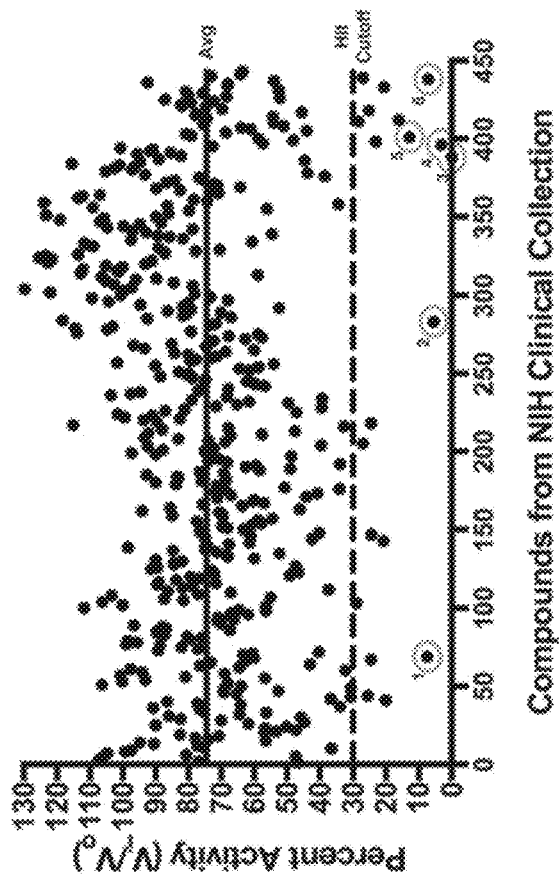
FIG. 12A shows the percent activity of EgtD screened against the NIH clinical collection.

In one non-limiting example, EgtD was screened against the NIH Clinical Collection, an accumulation of 446 compounds that have previously been used in human clinical drug trials. EgtD is an attractive drug target because it has been shown to be required for the biosynthesis of ergothioneine as well as being essential for the growth of M. tb in murine macrophages and animal models. Analysis of the 446 compounds screened from the NIH clinical collection, using the procedure of Example 10, below, yielded a hit cut-off of 30.1% activity of EgtD, where the definition of a hit is 3 standard deviations from the mean activity, as described above. Screening the entire collection produced an initial hit rate of 4.3% (19 compounds, FIG. 12A).

The preliminary 19 hits from the primary screen were validated by determining if the observed decrease in activity was reproducible and if the small molecules exhibited a dose-response relationship to EgtD. Additionally, despite using AdoHcy-TAMRA as the fluorescent probe, inspection of the high-throughput screening data demonstrated 3 compounds interfering with the competitive FP assay by either significantly decreasing the signal window or containing similar fluorescent properties as the fluorophore. Thus, out of the 19 hits, 6 compounds reproducibly decreased the activity of EgtD below the hit cut-off, as well as demonstrated a dose-response to EgtD (FIG. 12B), concluding a final hit rate of 1.4% for screening of the NIH clinical collection.

Although examination of EgtD required AdoMet concentrations only 500 nM in order to perform the high-throughput screening, it should be noted that as the concentration of AdoMet increases within the reaction, there will likely be a decrease in hit rates from identifying compounds that bind weakly to the enzyme of interest. Thus, in some embodiments, the concentration of AdoMet in a reaction is less than about 5 µM. In further embodiments, the concentration of AdoMet is less than about 2.5 µM.

In light of the robustness, high sensitivity, and relative simplicity and cost-effectiveness of the competitive FP assays of the present invention, pre-mixed kits can be utilized to further reduce the time and complexity of quantifying adenosine-containing compounds in a large number of reaction mixtures, particularly at concentrations in which the presence of adenosine-containing compounds can be distinguished from other compounds. Consequently, in some embodiments, the invention provides a kit for quantifying adenosine-containing compounds, comprising an inactivated MTAN enzyme comprising the amino acid sequence of SEQ ID NO: 1 and a fluorescent probe comprising an AdoHcy molecule amide-linked to a TAMRA fluorophore at the AdoHcy's α-amino position. In further embodiments, the MTAN-D198N enzyme and the fluorescent probe are provided together a single reaction mixture comprising the protein-probe complex. In other further embodiments, the MTAN-D198N enzyme and the fluorescent probe are provided as separate compositions.

In another embodiment, kits for quantifying adenosine-containing compounds within an aqueous composition or reaction mixture can comprise: (a) a fluorescent probe comprising an adenosine scaffold comprising an adenine moiety and a ribosyl moiety, and a TAMRA fluorophore, wherein the adenosine scaffold is covalently bound to the fluorophore by a linking portion comprising a linear chain of six or more atoms extending from the 5'-carbon of the ribosyl moiety to the 5-carboxyl functional group within TAMRA; and (b) a mutated MTAN enzyme, wherein the mutated MTAN enzyme comprises a mutation within the active site from an aspartic acid residue to an asparagine residue. In further embodiments, the mutated MTAN enzyme comprises an amino acid sequence selected from the group consisting of SEQ ID NO: 1, SEQ ID NO: 4, SEQ ID NO: 6, and SEQ ID NO: 8. In other further embodiments, the adenosine scaffold is AdoHcy, and the 5-carboxyl functional group of TAMRA is covalently bound to the α-amino moiety within AdoHcy. In even further embodiments, the kit comprises an MTAN-D198N enzyme comprising the amino acid sequence of SEQ ID NO: 1, and a fluorescent probe comprising an AdoHcy molecule amide-linked to a TAMRA fluorophore at the AdoHcy's α-amino position.

In another embodiment, the kit further comprises at least one small-molecule inhibitor candidate. In further embodiments, each small-molecule inhibitor candidate can comprise any synthesizable molecule less than about 1,000 Daltons. In even further embodiments, each small-molecule inhibitor candidate is an organic molecule. In still further embodiments, each small-molecule inhibitor candidate has been used previously in an animal or human clinical drug trial. In even still further embodiments, each small-molecule inhibitor candidate is a commercially-available drug.

In another embodiment, the kit further comprises an FP or FRET-compatible microplate comprising at least one reaction well. In further embodiments, the FP or FRET-compatible microplate is a black-well plate. In even further embodiments, the black-well plate comprises at least 6, 12, 24, 48, 96, or 384 reaction wells, up to at least 1536 reaction wells.

In other embodiments, each reaction well within the FP-compatible reaction plate contains at least one of the group consisting of MTAN-D198N, AdoHcy-TAMRA, a protein-probe complex, or a small-molecule inhibitor candidate.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. Thus, while the present invention has been described above with particularity, the following examples provide further detail in connection with what are presently deemed to be the most practical and preferred embodiments of the invention.

Example 1: Synthesis of D198N-MTAN

Site directed mutagenesis was performed on a pET-32 plasmid containing the pfs gene to create the HpMTAN variant (SEQ ID NO: 2). After confirming the presence of the D198N mutation, the pET-32 HpMTAN variant plasmid was used to transform BL21 (DE3) Rosetta cells. The newly transformed Rosetta cells were grown in LB media containing 0.1 mM chloramphenicol and 0.3 mM ampicillin at 37° C. Once the cell culture reached an $OD_{600}$ of 0.6-0.8, the temperature was decreased to 16° C. followed by the addition of 0.1 mM IPTG and incubated overnight. The cells were pelleted and resuspended in a 5 mM β-mercaptoethanol, 5 mM imidazole, 500 mM NaCl and 100 mM HEPES pH 7.5 buffer. The resuspended cells were lysed with DNase and Lysozyme on ice followed by sonication. The bacterial lysate was centrifuged at 15,000×g, and the supernatant was applied to a 5 mL HiTrap TALON Crude column. The column containing HpMTAN-D198N was washed with a buffer identical to the resuspension buffer, and was eluted from the HiTrap column using a linear gradient of 5 mM to 150 mM imidazole. The eluted HpMTAN-D198N was then dialyzed overnight in the resuspension buffer containing Human rhinovirus 3C protease that removes the thioredoxin poly-Histidine tag from HpMTAN-D198N. The protein sample was then reapplied to the 5 mL HiTrap TALON Crude column to remove the poly-Histidine-Thioredoxin tag. The concentration of the purified HpMTAN-D198N was measured using the Bradford assay.

Example 2: Synthesis of the AdoHcy-TAMRA Fluorescent Probe

Figure 13:
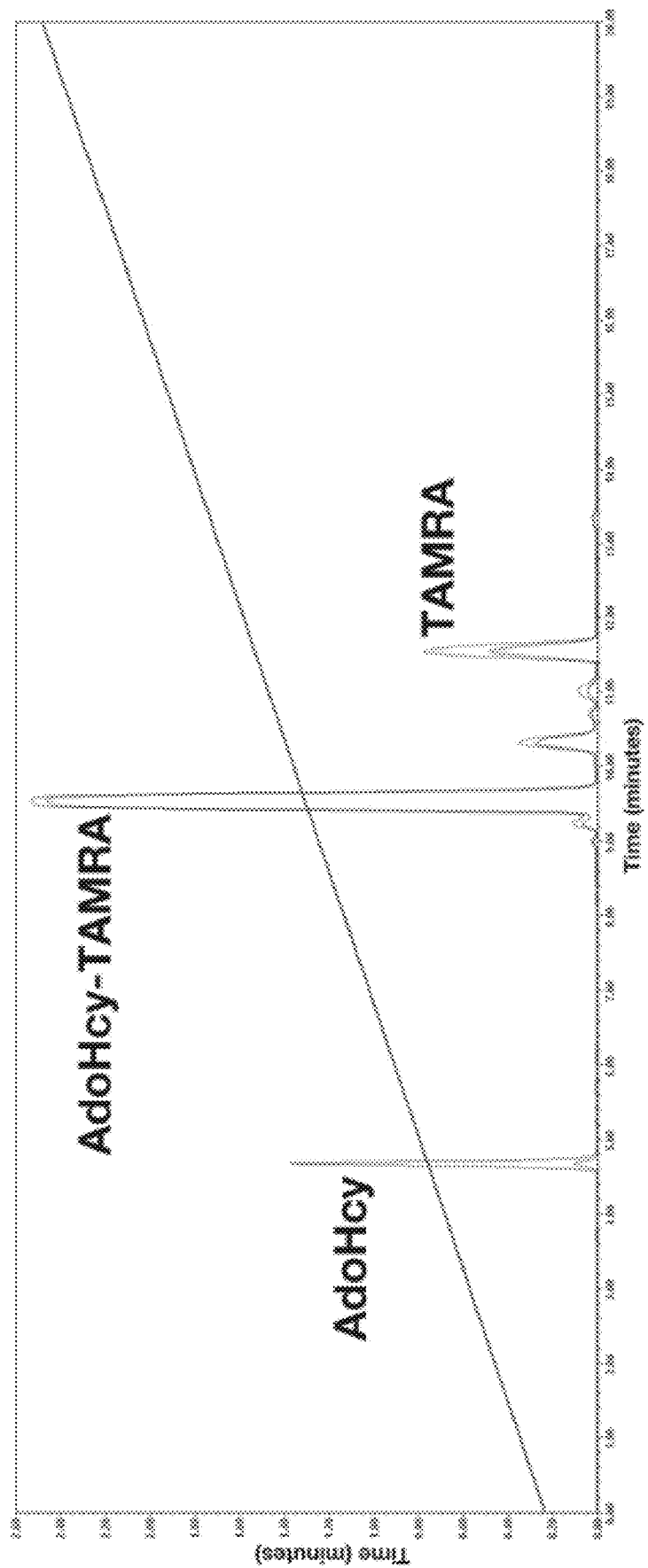
FIG. 13 shows an HPLC chromatogram of the AdoHcy-TAMRA reaction mixture.
Figure 14:
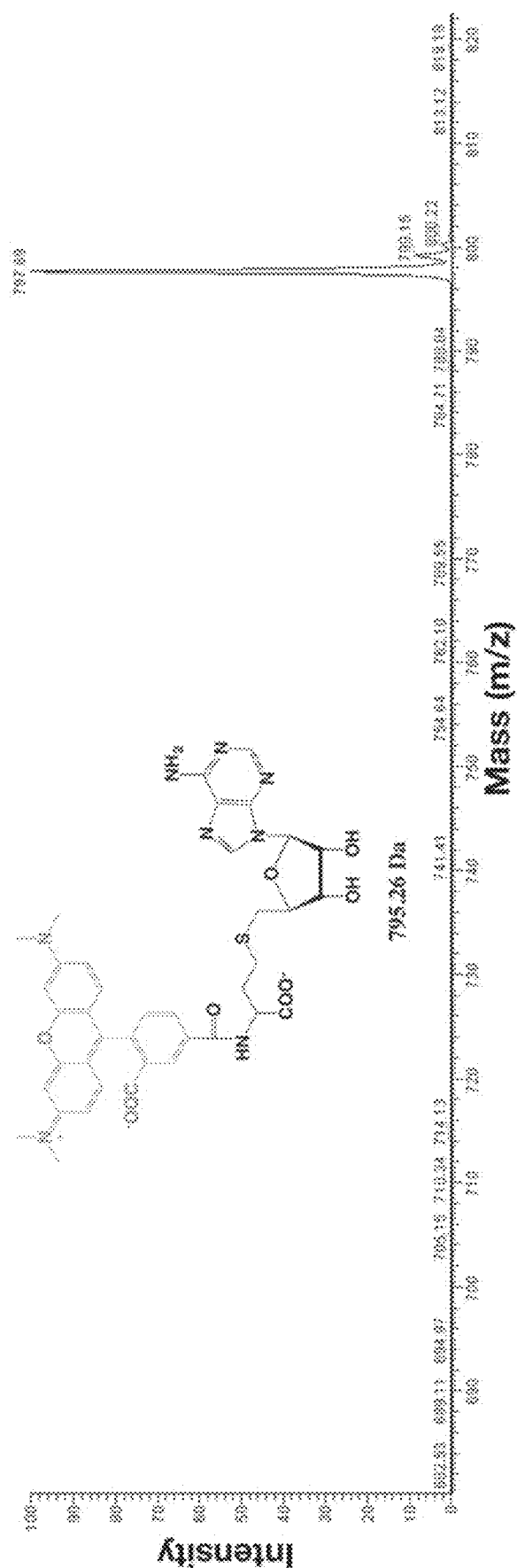
FIG. 14 shows an ESI-MS spectrum of the AdoHcy-TAMRA fluorescent probe.

One-pot synthesis of the fluorescent probe was performed by combining AdoHcy (1.3 mg, Sigma) in a 100-mM sodium bicarbonate buffer at pH 9 with 5-carboxytetramethylrhodamine succinimidyl ester (SE-TAMRA, 1.0 mg, Setareh Biotech) in 100% DMSO (FIG. 3). The reaction was incubated overnight at room temperature protected from light to avoid photobleaching of the fluorophore. The resulting product was purified by reverse-phase HPLC (Waters 2487) using a linear gradient consisting of 0.1% trifluoroacetic acid and acetonitrile on an analytical C18 column. Elution of AdoHcy-TAMRA and AdoHcy were monitored spectroscopically at the absorption maximum of the fluorophore (545 nm) and the adenine moiety of AdoHcy (260 nm) using a dual wavelength detector (Waters 2487 Dual k Absorbance Detector). Eluted compounds demonstrating absorption at both wavelengths were collected and further characterized using ESI-MS (Finnigan LC-Q-Deca) in positive ion mode. The synthesized AdoHcy-TAMRA probe was separated from the reaction mixture using reverse phase HPLC (FIG. 13), and the appropriate eluting peak was immediately validated by ESI-MS providing the expected mass of 797.69 Da (FIG. 14).

Example 3: Equilibrium Binding Studies Between MTAN-D198N and AdoHcy-TAMRA

All FP assays used to conduct equilibrium binding studies between MTAN-D198N and AdoHcy-TAMRA were performed using a Biotek Synergy H4 Hybrid Reader to measure the parallel ($F_\parallel$) and perpendicular ($F_\perp$) fluorescence intensities, which were then used to calculate the mP value according to Equation 1, below.

$$mP = 1000 \times \frac{(F_\parallel - F_\perp)}{(F_\parallel + F_\perp)} \quad \text{(Equation 1)}$$

MTAN-D198N and AdoHcy-TAMRA were synthesized according to the procedures in Example 1 and Example 2, respectively. The protein-probe complex for performing the equilibrium binding FP experiments between MTAN-D198N and AdoHcy-TAMRA were incubated for 10 minutes at ambient temperature prior to measuring the fluorescence intensities. Equilibrium binding experiments to determine the $K_d$ value for the MTAN-D198N/AdoHcy-TAMRA complex were performed using 5 nM of AdoHcy-TAMRA with varying concentrations of MTAN-D198N in 50 mM HEPES at pH 7.5. The resulting data were fitted to a one site—total binding equation in Prism 7 (GraphPad Software, San Diego, CA) where $mP_{max}$ represents the maximum fluorescent polarization signal, NS is the slope for nonspecific binding of the fluorescent probe, [Protein] is the concentration of MTAN-D198N, and $mP_{min}$ is the minimum fluorescent polarization signal, according to Equation 2 below. The generated binding isotherm demonstrates that the AdoHcy-TAMRA fluorescent probe possesses high affinity to MTAN-D198N, exhibiting a determined $K_d$ value of 11.3±0.7 nM (FIG. 4).

$$mP = \left(\frac{mP_{max} \times [\text{Protein}]}{K_d + [\text{Protein}]}\right) + (NS \times [\text{Protein}]) + mP_{min} \quad \text{(Equation 2)}$$

Example 4: Assessment of the Reproducibility of the Competitive FP Assay

Assessment of the reproducibility of competitive FP assays according to the present invention was conducted in the same Biotek Synergy H4 Hybrid Reader as described above in Example 3. Thirteen positive control reactions and thirteen negative control reactions were conducted in order to calculate a Z'-factor, according to Equation 3 below, where σ represents the standard deviation of the observed values, represents the mean observed value, and Pos and Neg represent the positive and negative control reaction, respectively.

$$Z' = 1 - \frac{3\sigma_{Pos} + 3\sigma_{Neg}}{|\mu_{Pos} - \mu_{Neg}|} \quad \text{(Equation 3)}$$

Each positive control reaction contained 50 nM of MTAN-D198N and 11.3 nM of AdoHcy-TAMRA. Each negative control reaction contained 11.3 nM of AdoHcy-TAMRA. Positive and negative reactions both contained 50 µL reaction volumes. Fluorescence polarization was measured after 10 minutes of incubation at room temperature. Observed values were used to calculate the mean and standard deviation of the Z'-factor. The calculated Z'-factor was 0.77.

Example 5: Determination of the Limit of Detection and Inhibitory Constants of Adenosine-Containing Compounds Competitive FP assays to quantify adenosine-containing compounds were carried out in 50 µL reactions using the same Biotek Synergy H4 Hybrid Reader as described above in Example 3, with concentrations of AdoHcy-TAMRA and MTAN-D198N as described above in Example 4. Varying concentrations of AdoHcy, AdoMet, and MTA were added to each reaction in order to assess the $K_i$ value for each compound. Observed polarization values were fitted into a one site—fit $K_i$ equation (Equation 4 below) to determine an $EC_{50}$ value using Equation 5, using the Prism 7 software program (GraphPad Software, San Diego, CA). In Equations 5 and 6, $EC_{50}$ refers to the half maximal effective concentration and [ligand] refers to the concentration of the adenosine-containing compound.

$$mP = mP_{min} + \frac{(mP_{max} - mP_{min})}{(1 + 10^{[Ligand] - Log\ EC_{50}})} \quad \text{(Equation 5)}$$

$$Log\ EC_{50} = Log\left(10^{Log\ K_i} \times \left(1 + \frac{[\text{Probe}]}{K_d}\right)\right) \quad \text{(Equation 6)}$$

The $K_i$ values determined for MTA, AdoHcy, and AdoMet were 24.2±1.2, 29.5±3.6 nM, and 989±160 nM, respectively. Generated displacement curves used to determine the $K_i$ for MTA and AdoHcy are shown in FIG. 5. The generated displacement curve used to determine the $K_i$ for AdoMet is shown in FIG. 6A, and is superimposed with a displacement curve for AdoHcy for comparison. The limit of detection for MTA, AdoHcy, and AdoMet were 10 nM (about 5 pmol), 6 nM (about 0.3 pmol), and 312 nM, respectively.

Example 6: Evaluation of the Effect of Background AdoMet when Quantifying AdoHcy In order to evaluate the ability of the competitive FP assay to quantify AdoHcy in the presence of AdoMet, multiple displacement curves of AdoHcy were generated according to the procedure of Example 5, in the presence of varying concentrations of AdoMet. Displacement curves were generated by plotting the observed polarization data at each concentration of AdoMet as a function of AdoHcy concentration according to Equation 5, as shown in FIG. 6B.

Example 7: Expression and Purification of EgtD

The gene encoding EgtD from *Mycobacterium tuberculosis* was codon-optimized for expression in *Escherichia coli*. The codon-optimized egtD gene was then inserted into a pET32 based plasmid containing a N-terminal poly-Histidine tag using the Gibson Assembly method and validated by sequencing. The EgtD construct was used to transform component T7 Express cells, and grown in LB media containing 0.3 mM carbenicillin at 37° C. Once the cell culture reached an $OD_{600}$ of 0.6-0.8, the temperature was decreased to 16° C. followed by the addition of 0.1 mM IPTG and incubated overnight. After pelleting the cell culture the next day, the cell pellet was resuspended in a buffer containing 0.3 M sodium chloride, 5 mM imidazole and 30 mM TRIS at pH 8.0. Purification of EgtD from the resuspended cells was then performed similarly to HpMTAN-D198N as described above in Example 1.

Example 8: Determination of Apparent Steady-State Kinetic Parameters of EgtD Determining the $K_m^{app}$ of L-histidine for the purified EgtD using the developed competitive FP assay was performed at 25° C. The assay components consisted of 50 nM HpMTAN-D198N, 11.3 nM AdoHcy-TAMRA, and 5 nM EgtD in 25 mM TRIS at pH 8.0. A stock solution of L-histidine was serially diluted in the kinetic reactions to provide a concentration range from 0.05 to 3.00 mM. The kinetic reactions were initiated by the addition of 500 nM of AdoMet, and the rate of catalysis of EgtD was continuously monitored by observing a decrease in the mP value using the same Biotek Synergy H4 Hybrid Reader as described above in Example 3. Conversion of the observed initial velocities into [AdoHcy]/minute was calculated using a standard curve of AdoHcy in the presence of 500 nM AdoMet (FIG. 8). The resulting data were fitted to the Michaelis-Menten equation, exhibited by Equation 7, below, using Prism 7 for calculating $K_m^{app}$ of L-histidine for EgtD.

$$V_o = \frac{V_{max} \times [\text{Histidine}]}{K_m + [\text{Histidine}]} \quad \text{(Equation 7)}$$

Example 9: Characterization of Calf Intestinal Alkaline Phosphatase

Calf Intestinal Alkaline Phosphatase (CIAP) was obtained from New England Biolabs. The procedure was identical to the procedure in Example 8 used to determine the kinetic parameters of EgtD, except that each reaction mixture contained 50 nM HpMTAN-D198N, 11.3 nM AdoHcy-TAMRA, and 0.25 U/mL of CIAP in 25 mM TRIS at pH 8.0. Reactions were initiated by adding ATP at varying concentrations ranging from 0.1 to 20 µM. Due to the ability of ATP to act as an inhibitor of CIAP at high concentrations, steady-state analysis of the resulting data was fitted to a substrate-inhibition equation in Equation 8, below, using Prism 7.

$$V_o = \frac{V_{max} \times [ATP]}{K_m + [ATP]\frac{1+[ATP]}{K_i}} \quad \text{(Equation 8)}$$

Example 10: High-Throughput Screening of Small Molecule Inhibitors Against EgtD The activity of EgtD was screened against the NIH Clinical Collection, which contains 446 compounds that were dissolved in 100% DMSO to provide a stock concentration of 10 mM for each compound. Screening consisted of adding 48.5 µL of an assay mixture (51.5 nM HpMTAN-D198N, 11.6 nM AdoHcy-TAMRA, 11.1 nM EgtD, 773 µM L-histidine, and 51.5 mM TRIS at pH 8.0) to a 384-well black well plate, followed by the addition 0.5 µL of each tested compound (100 µM, and 1% DMSO) to each well. The reactions were initiated with 1 µL of AdoMet (500 nM) and the rate of all reactions for EgtD were monitored continuously. Screening hits were validated assessing the inhibitor dose-response to EgtD by serially diluting the compound of interest and performing the assay as described in Example 5.

Additionally, similar to the method described above in Example 4, the reproducibility of the developed competitive FP assay for monitoring the activity of EgtD was assessed by calculating the value (Equation 3) using 13 positive and negative replicates. The calculated Z'-factor was 0.56.

Example 11: Synthesis of E12C and E213C Variants of D198N-MTAN

A study is conducted in accordance with embodiments of the present invention to synthesize variants of D198N-MTAN that contain a glutamic acid to cysteine mutation at the periphery of the enzyme and proximal to the AdoHcy binding site, comprising the amino acid sequence of SEQ ID NO: 4, SEQ ID NO: 6, and variants of SEQ ID NO: 8 in which a cysteine residue is selected at either residue 12 or residue 213. The same procedure is used as in the production of D198N-MTAN in Example 1, except that dithiothreitol (2 mM) or TCEP (0.5 mM) is included in all culture media or buffer conditions. It is expected that mutated MTAN enzymes comprising the amino acid sequence of SEQ ID NO: 4, SEQ ID NO: 6, or SEQ ID NO: 8 are made at a similar purity and concentration as the D198N-MTAN variant of Example 1.

Example 12: Synthesis of E12C or E213C Conjugates of MTAN with a Secondary Fluorophore A study is conducted in accordance with embodiments of the present invention to produce E12C or E213C conjugates with a secondary fluorophore. HpMTAN variants containing D198N mutations along with E12C and/or E213 mutations are combined with a secondary fluorophore covalently bound to a thiol-reactive functional group, for example, QSY™ 7 $C_5$-Maleimide (ThermoFisher) using commonly-known techniques for reacting thiols with biomolecules, specific to the particular thiol-reactive functional group associated with the chosen secondary fluorophore. Excess, non-reacted secondary fluorophore is removed using dialysis or buffer exchange with ultrafiltration. The concentration of the modified MTAN variant conjugated to the secondary fluorophore is assessed by measuring the absorbance of the protein. Conjugation to the secondary fluorophore is confirmed by mass spectrometry. It is expected that E12C or E213C variants that are conjugated to a secondary fluorophore will be produced in a purity and concentration sufficient to carry out subsequent FRET-based quantification of adenosine-containing compounds in accordance with methods of the present invention.

Example 13: FRET-Based Quantification of Adenosine-Containing Compounds

A study is conducted in accordance with embodiments of the present invention to assess the viability of FRET-based quantification methods. To assess binding of AdoHcy-TAMRA to the QSY™ 7 $C_5$-Maleimide modified MTAN-D198N-E12 (SEQ ID NO: 4) and MTAN-D198N-E213 variants, referred to as E12C* and E213*, respectively, titration experiments using fixed concentrations of AdoHcy-TAMRA and increasing concentrations of E12C* or E213C* are performed. The loss of fluorescence due to complex formation and subsequent fluorescence quenching indicates complex formation. From these experiments, the Kd value for the respective complexes is determined and compared to the known affinity of the AdoHcy-TAMRA to MTAN-D198N determined in Example 3. If either of these two variants afford Kd values below 30 nM, further control studies are performed to assess utility of the complex in FRET-based displacement assays in a 384-well microplate format. An example of a control study includes titrating a complex of E12C*/AdoHcy-TAMRA at a known concentration with AdoHcy to promote release of AdoHcy-TAMRA from E12C*. The subsequent increase in relative fluorescence due to disruption of the FRET pair is monitored by measuring the increase in relative fluorescence. Similar experiments are performed with each of the possible product analytes (Adenosine, 5'-Deoxyadenosine, 5'-Deoxy-5'-methylthioadenosine) as well as AdoMet to assess affinity of these compounds to the protein component of the FRET probe. It is expected that the FRET-based assay will have a Kd value below 30 nM and be suitable for assessing the progress of reactions of AdoMet-dependent and ATP-dependent reactions.

---

I claim:

1. A method for quantifying adenosine-containing compounds within an aqueous composition comprising the steps of:
   a) providing a fluorescent probe comprising:
      i) an adenosine scaffold comprising S-adenosyl homocysteine (AdoHcy), and
      ii) a 5-carboxytetramethylrhodamine (TAMRA) fluorophore;
      wherein the 5-carboxyl functional group within the TAMRA fluorophore is covalently bound to the α-amino moiety within AdoHcy;
   b) providing a mutated *Helicobacter pylori* (Hp) 5'-methylthioadenosine/S-adenosyl homocysteine nucleosidase (MTAN enzyme), wherein the mutated MTAN enzyme comprises an amino acid sequence selected from the group consisting of:
      i) SEQ ID NO: 4, wherein the cysteine residue at position 12 is conjugated to a secondary fluorophore,
      ii) SEQ ID NO: 6, wherein the cysteine residue at position 213 is conjugated to a secondary fluorophore, and
      iii) SEQ ID NO: 8, wherein the amino acid residue at one or both of positions 12 and 213 is a cysteine residue conjugated to a secondary fluorophore, and
      wherein the secondary fluorophore consists of DABCYL-maleimide or C5-maleimide;
      wherein the secondary fluorophore conjugated to any of the mutated MTAN enzymes comprises a fluorescently-active moiety and a thiol-reactive crosslinker that bridges the fluorescently-active moiety to the cysteine residue;
   c) forming a protein-probe complex between the mutated MTAN enzyme and the fluorescent probe;
   d) measuring the fluorescence intensity of the fluorescent probe within the protein-probe complex;
   e) combining an adenosine-containing compound, the adenosine-containing compound selected from the group consisting of AdoHcy, 5'-methylthioadenosine, adenosine diphosphate, adenosine monophosphate, and adenosine, with the protein-probe complex to form an adenosine quantification mixture;
   f) measuring the increase of fluorescence intensity of the fluorescent probe in the presence of the adenosine quantification mixture; and
   g) calculating the amount of the adenosine-containing compound within the adenosine quantification mixture using the increase of fluorescence intensity of the fluorescent probe in the presence of the adenosine quantification mixture.

2. The method according to claim 1, wherein the method further comprises the step of synthesizing the fluorescent probe, the synthesis comprising the steps of: incubating AdoHcy with a stoichiometric amount of SE-TAMRA for at least 10 minutes and up to 60 minutes, and initiating a nucleophilic attack of the succinimidyl ester within SE-TAMRA by the α-amino group of AdoHcy, thereby forming an amide linkage between TAMRA and AdoHcy.

3. The method according to claim 1, wherein the cross-linker comprises a maleimide group.

4. The method according to claim 1, wherein the method further comprises the steps of: synthesizing the adenosine-containing compound by combining within a reaction mixture at least one supplemental enzyme and at least one supplemental starting material that react to form an adenosine-containing compound as a product; and combining the reaction mixture containing the adenosine-containing compound product with the protein-probe complex.

5. The method according to claim 4, wherein the at least one supplemental enzyme comprises an enzyme selected from the group consisting of an AdoMet-dependent enzyme and an ATP-dependent enzyme.

6. The method according to claim 5, wherein the at least one supplemental enzyme comprises a methyltransferase enzyme, and the at least one supplemental starting material comprises AdoMet, wherein the concentration of the AdoMet within the reaction mixture is less than about 5 µM.

7. The method according to claim 5, wherein the at least one supplemental enzyme comprises an ATP-dependent kinase enzyme, and the at least one supplemental starting material comprises ATP.

8. The method according to claim 1, wherein the reaction mixture further comprises at least one small-molecule inhibitor candidate, wherein each small-molecule inhibitor candidate is less than about 1,000 Daltons.

9. A protein-probe complex comprising a mutated Hp-MTAN enzyme and a fluorescent probe wherein:
   a) the mutated MTAN enzyme comprises an amino acid sequence selected from the group consisting of:

SEQ ID NO: 4, wherein the cysteine residue at position 12 is conjugated to a secondary fluorophore, SEQ ID NO: 6, wherein the cysteine residue at position 213 is conjugated to a secondary fluorophore, and SEQ ID NO: 8, wherein the amino acid reside at one or both of positions 12 and 213 is a cysteine residue conjugated to a secondary fluorophore;

wherein the secondary fluorophore consists of DABCYL-maleimide or C5-maleimide; and wherein the secondary fluorophore conjugated to any of the mutated MTAN enzymes comprises a fluorescently-active moiety and a thiol-reactive crosslinker that bridges the fluorescently-active moiety to the cysteine residue; and b) the fluorescent probe comprises an adenosine scaffold comprising AdoHcy and a TAMRA fluorophore, wherein the 5-carboxyl functional group within the TAMRA fluorophore is covalently bound to the α-amino moiety within AdoHcy.

* * * * *

UNITED STATES PATENT AND TRADEMARK OFFICE
CERTIFICATE OF CORRECTION

Page 1 of 1

PATENT NO. : 12,018,299 B2
APPLICATION NO. : 16/956435
DATED : June 25, 2024
INVENTOR(S) : Donald R. Ronning It is certified that error appears in the above-identified patent and that said Letters Patent is hereby corrected as shown below:

In the Specification

Column 15, Line 30, delete "low p M" and replace with --low µM--.

In the Claims

Column 28, Line 33, delete "(Equation 4 below)".

Column 28, Line 34, delete "Equation 5" and replace with --Equation 4--.

Column 28, Line 36, delete "5 and 6" and replace with --4 and 5--.

Column 28, Line 42, delete "(Equation 5)" and replace with --(Equation 4)--.

Column 28, Line 44, delete "(Equation 6)" and replace with --(Equation 5)--.

Column 28, Line 67, delete "Equation 5" and replace with --Equation 4--.

Column 29, Line 38, delete "Equation 7" and replace with --Equation 6--.

Column 29, Line 42, delete "(Equation 7)" and replace with --(Equation 6)--.

Column 29, Line 59, delete "Equation 8" and replace with --Equation 7--.

Column 29, Line 63, delete "(Equation 8)" and replace with --(Equation 7)--.

Signed and Sealed this
First Day of July, 2025

Coke Morgan Stewart
*Acting Director of the United States Patent and Trademark Office*

SEQUENCE LISTING

<160> NUMBER OF SEQ ID NOS: 8

<210> SEQ ID NO 1
<211> LENGTH: 230
<212> TYPE: PRT
<213> ORGANISM: Artificial Sequence
<220> FEATURE:
<223> OTHER INFORMATION: Amino acid sequence for MTAN-D198N mutant

<400> SEQUENCE: 1

```
Met Gln Lys Ile Gly Ile Leu Gly Ala Met Arg Glu Glu Ile Thr Pro
1               5                   10                  15

Ile Leu Glu Leu Phe Gly Val Asp Phe Glu Glu Ile Pro Leu Gly Gly
            20                  25                  30

Asn Val Phe His Lys Gly Val Tyr His Asn Lys Glu Ile Ile Val Ala
        35                  40                  45

Tyr Ser Lys Ile Gly Lys Val His Ser Thr Leu Thr Thr Ser Met
    50                  55                  60

Ile Leu Ala Phe Gly Val Gln Lys Val Leu Phe Ser Gly Val Ala Gly
65                  70                  75                  80

Ser Leu Val Lys Asp Leu Lys Ile Asn Asp Leu Leu Val Ala Thr Gln
                85                  90                  95

Leu Val Gln His Asp Val Asp Leu Ser Ala Phe Asp His Pro Leu Gly
            100                 105                 110

Phe Ile Pro Glu Ser Ala Ile Phe Ile Glu Thr Ser Gly Ser Leu Asn
        115                 120                 125

Ala Leu Ala Lys Lys Ile Ala Asn Glu Gln His Ile Ala Leu Lys Glu
    130                 135                 140

Gly Val Ile Ala Ser Gly Asp Gln Phe Val His Ser Lys Glu Arg Lys
145                 150                 155                 160

Glu Phe Leu Val Ser Glu Phe Lys Ala Ser Ala Val Glu Met Glu Gly
                165                 170                 175

Ala Ser Val Ala Phe Val Cys Gln Lys Phe Gly Val Pro Cys Cys Val
            180                 185                 190

Leu Arg Ser Ile Ser Asn Asn Ala Asp Glu Lys Ala Gly Met Ser Phe
        195                 200                 205

Asp Glu Phe Leu Glu Lys Ser Ala His Thr Ser Ala Lys Phe Leu Lys
    210                 215                 220
```

Ser Met Val Asp Glu Leu
225                 230

<210> SEQ ID NO 2
<211> LENGTH: 693
<212> TYPE: DNA
<213> ORGANISM: Artificial Sequence
<220> FEATURE:
<223> OTHER INFORMATION: Polynucleotide sequence encoding for MTAN-D198N
      mutant

<400> SEQUENCE: 2

```
atgcaaaaaa ttggcatttt aggggcgatg agagaagaaa taaccccctat actagaattg    60
tttggcgtgg attttgaaga gatcccttta gggggaatg ttttccataa aggcgtttat    120
cataataagg aaatcattgt cgcttatagc aagattggca aggtgcattc cactttaacc    180
acaacaagca tgattttagc gtttggcgtt cagaaggtgc tttttagcgg ggtggctgga    240
agcttagtta agatttaaa atcaatgat ttgttagtgg ctactcaatt agtccagcac    300
gatgtggatt tgagcgcgtt tgatcaccct ttagggttta tccccgaaag cgcgattttt    360
attgaaacga gtggaagttt aaacgcttta gctaaaaaga tcgctaatga gcaacatatc    420
gcgctcaaag aaggcgtcat cgcatcaggc gatcagtttg tgcatagcaa agaaaggaaa    480
gaatttttag ttagcgagtt taaagcgagc gcggtggaaa tggaggggc gagcgtggcg    540
tttgtgtgcc aaaaatttgg cgtgccatgc tgcgtgctaa ggagcattag caataacgcc    600
gatgaaaaag ccggtatgag ttttgatgaa ttttagaaa aaagcgctca cacttcagcg    660
aaattcttaa aaagcatggt ggatgagctt tag                                  693
```

<210> SEQ ID NO 3
<211> LENGTH: 693
<212> TYPE: DNA
<213> ORGANISM: Helicobacter pylori

<400> SEQUENCE: 3

```
atgcaaaaaa ttggcatttt aggggcgatg agagaagaaa taaccccctat actagaattg    60
tttggcgtgg attttgaaga gatcccttta gggggaatg ttttccataa aggcgtttat    120
cataataagg aaatcattgt cgcttatagc aagattggca aggtgcattc cactttaacc    180
acaacaagca tgattttagc gtttggcgtt cagaaggtgc tttttagcgg ggtggctgga    240
agcttagtta agatttaaa atcaatgat ttgttagtgg ctactcaatt agtccagcac    300
gatgtggatt tgagcgcgtt tgatcaccct ttagggttta tccccgaaag cgcgattttt    360
attgaaacga gtggaagttt aaacgcttta gctaaaaaga tcgctaatga gcaacatatc    420
gcgctcaaag aaggcgtcat cgcatcaggc gatcagtttg tgcatagcaa agaaaggaaa    480
gaatttttag ttagcgagtt taaagcgagc gcggtggaaa tggaggggc gagcgtggcg    540
tttgtgtgcc aaaaatttgg cgtgccatgc tgcgtgctaa ggagcattag cgataacgcc    600
gatgaaaaag ccggtatgag ttttgatgaa ttttagaaa aaagcgctca cacttcagcg    660
aaattcttaa aaagcatggt ggatgagctt tag                                  693
```

<210> SEQ ID NO 4
<211> LENGTH: 230
<212> TYPE: PRT
<213> ORGANISM: Artificial Sequence
<220> FEATURE:
<223> OTHER INFORMATION: Amino acid sequence for D198N-MTAN-E13C variant

<400> SEQUENCE: 4

```
Met Gln Lys Ile Gly Ile Leu Gly Ala Met Arg Cys Glu Ile Thr Pro
1               5                   10                  15

Ile Leu Glu Leu Phe Gly Val Asp Phe Glu Ile Pro Leu Gly Gly
            20                  25                  30

Asn Val Phe His Lys Gly Val Tyr His Asn Lys Glu Ile Ile Val Ala
        35                  40                  45

Tyr Ser Lys Ile Gly Lys Val His Ser Thr Leu Thr Thr Thr Ser Met
50                  55                  60

Ile Leu Ala Phe Gly Val Gln Lys Val Leu Phe Ser Gly Val Ala Gly
65                  70                  75                  80

Ser Leu Val Lys Asp Leu Lys Ile Asn Asp Leu Leu Val Ala Thr Gln
                85                  90                  95

Leu Val Gln His Asp Val Asp Leu Ser Ala Phe Asp His Pro Leu Gly
            100                 105                 110

Phe Ile Pro Glu Ser Ala Ile Phe Ile Glu Thr Ser Gly Ser Leu Asn
            115                 120                 125

Ala Leu Ala Lys Lys Ile Ala Asn Glu Gln His Ile Ala Leu Lys Glu
        130                 135                 140

Gly Val Ile Ala Ser Gly Asp Gln Phe Val His Ser Lys Glu Arg Lys
145                 150                 155                 160

Glu Phe Leu Val Ser Glu Phe Lys Ala Ser Ala Val Glu Met Glu Gly
                165                 170                 175

Ala Ser Val Ala Phe Val Cys Gln Lys Phe Gly Val Pro Cys Cys Val
            180                 185                 190

Leu Arg Ser Ile Ser Asn Asn Ala Asp Glu Lys Ala Gly Met Ser Phe
        195                 200                 205

Asp Glu Phe Leu Glu Lys Ser Ala His Thr Ser Ala Lys Phe Leu Lys
210                 215                 220

Ser Met Val Asp Glu Leu
225                 230

<210> SEQ ID NO 5
<211> LENGTH: 693
<212> TYPE: DNA
<213> ORGANISM: Artificial Sequence
<220> FEATURE:
<223> OTHER INFORMATION: Polynucleotide sequence encoding for MTAN-
      D198N-E13C variant
<220> FEATURE:
<221> NAME/KEY: misc_feature
<222> LOCATION: (36)..(36)
<223> OTHER INFORMATION: n is thymine or cytosine

<400> SEQUENCE: 5
atgcaaaaaa ttggcatttt agggcgatg agatgngaaa taacccctat actagaattg      60
tttggcgtgg attttgaaga datcccttta gggggaatg ttttccataa aggcgtttat     120
cataataagg aaatcattgt cgcttatagc aagattggca aggtgcattc cactttaacc    180
acaacaagca tgattttagc gtttggcgtt cagaaggtgc tttttagcgg ggtggctgga    240
agcttagtta aagatttaaa aatcaatgat ttgttagtgg ctactcaatt agtccagcac    300
gatgtggatt tgagcgcgtt tgatcaccct ttagggttta tccccgaaag cgcgattttt    360
attgaaacga gtggaagttt aaacgcttta gctaaaaaga tcgctaatga gcaacatatc    420
gcgctcaaag aaggcgtcat cgcatcaggc gatcagtttg tgcatagcaa agaaaggaaa    480 gaattttag ttagcgagtt taaagcgagc gcggtggaaa tggaggggc gagcgtggcg     540
```

```
tttgtgtgcc aaaaatttgg cgtgccatgc tgcgtgctaa ggagcattag caataacgcc    600
gatgaaaaag ccggtatgag ttttgatgaa ttttagaaaa aaagcgctca cacttcagcg    660
aaattcttaa aaagcatggt ggatgagctt tag                                 693
```

<210> SEQ ID NO 6
<211> LENGTH: 230
<212> TYPE: PRT
<213> ORGANISM: Artificial Sequence
<220> FEATURE:
<223> OTHER INFORMATION: Amino acid sequence for D198N-MTAN-E214C variant

<400> SEQUENCE: 6

```
Met Gln Lys Ile Gly Ile Leu Gly Ala Met Arg Glu Glu Ile Thr Pro
1               5                   10                  15
Ile Leu Glu Leu Phe Gly Val Asp Phe Glu Glu Ile Pro Leu Gly Gly
                20                  25                  30
Asn Val Phe His Lys Gly Val Tyr His Asn Lys Glu Ile Ile Val Ala
            35                  40                  45
Tyr Ser Lys Ile Gly Lys Val His Ser Thr Leu Thr Thr Ser Met
    50                  55                  60
Ile Leu Ala Phe Gly Val Gln Lys Val Leu Phe Ser Gly Val Ala Gly
65                  70                  75                  80
Ser Leu Val Lys Asp Leu Lys Ile Asn Asp Leu Leu Val Ala Thr Gln
                85                  90                  95
Leu Val Gln His Asp Val Asp Leu Ser Ala Phe Asp His Pro Leu Gly
            100                 105                 110
Phe Ile Pro Glu Ser Ala Ile Phe Ile Glu Thr Ser Gly Ser Leu Asn
        115                 120                 125
Ala Leu Ala Lys Lys Ile Ala Asn Glu Gln His Ile Ala Leu Lys Glu
    130                 135                 140
Gly Val Ile Ala Ser Gly Asp Gln Phe Val His Ser Lys Glu Arg Lys
145                 150                 155                 160
Glu Phe Leu Val Ser Glu Phe Lys Ala Ser Ala Val Glu Met Glu Gly
                165                 170                 175
Ala Ser Val Ala Phe Val Cys Gln Lys Phe Gly Val Pro Cys Cys Val
            180                 185                 190
Leu Arg Ser Ile Ser Asn Asn Ala Asp Glu Lys Ala Gly Met Ser Phe
        195                 200                 205
Asp Glu Phe Leu Cys Lys Ser Ala His Thr Ser Ala Lys Phe Leu Lys
    210                 215                 220
Ser Met Val Asp Glu Leu
225                 230
```

<210> SEQ ID NO 7
<211> LENGTH: 693
<212> TYPE: DNA
<213> ORGANISM: Artificial Sequence
<220> FEATURE:
<223> OTHER INFORMATION: Polynucleotide sequence encoding for MTAN-D198N-E214C variant
<220> FEATURE:
<221> NAME/KEY: misc_feature
<222> LOCATION: (639)..(639)
<223> OTHER INFORMATION: n is thymine or cytosine

<400> SEQUENCE: 7

```
atgcaaaaaa ttggcatttt aggggcgatg agagaagaaa taaccccctat actagaattg    60
```

```
tttggcgtgg attttgaaga gatccctttaa gggggaatg ttttccataa aggcgtttat    120
cataataagg aaatcattgt cgcttatagc aagattggca aggtgcattc cactttaacc    180
acaacaagca tgattttagc gtttggcgtt cagaaggtgc ttttagcgg ggtggctgga    240 agcttagtta aagatttaaa aatcaatgat ttgttagtgg ctactcaatt agtccagcac    300
gatgtggatt tgagcgcgtt tgatcaccct ttagggttta tccccgaaag cgcgattttt    360
attgaaacga gtggaagttt aaacgcttta gctaaaaaga tcgctaatga gcaacatatc    420
gcgctcaaag aaggcgtcat cgcatcaggc gatcagtttg tgcatagcaa agaaaggaaa    480 gaattttttag ttagcgagtt taaagcgagc gcggtggaaa tggagggggc gagcgtggcg    540
tttgtgtgcc aaaaatttgg cgtgccatgc tgcgtgctaa ggagcattag caataacgcc    600
gatgaaaaag ccggtatgag ttttgatgaa tttttatgna aaagcgctca cacttcagcg    660
aaattcttaa aaagcatggt ggatgagctt tag                                 693

<210> SEQ ID NO 8
<211> LENGTH: 230
<212> TYPE: PRT
<213> ORGANISM: Artificial Sequence
<220> FEATURE:
<223> OTHER INFORMATION: Amino acid sequence for D198N-MTAN-X variants
<220> FEATURE:
<221> NAME/KEY: MISC_FEATURE
<222> LOCATION: (12)..(12)
<223> OTHER INFORMATION: Xaa is glutamic acid or cysteine
<220> FEATURE:
<221> NAME/KEY: MISC_FEATURE
<222> LOCATION: (52)..(52)
<223> OTHER INFORMATION: Xaa is isoleucine, methionine, or arginine
<220> FEATURE:
<221> NAME/KEY: MISC_FEATURE
<222> LOCATION: (104)..(104)
<223> OTHER INFORMATION: Xaa is leucine, methionine, or arginine
<220> FEATURE:
<221> NAME/KEY: MISC_FEATURE
<222> LOCATION: (153)..(153)
<223> OTHER INFORMATION: Xaa is phenylalanine or arginine
<220> FEATURE:
<221> NAME/KEY: MISC_FEATURE
<222> LOCATION: (174)..(174)
<223> OTHER INFORMATION: Xaa is methionine or arginine
<220> FEATURE:
<221> NAME/KEY: MISC_FEATURE
<222> LOCATION: (213)..(213)
<223> OTHER INFORMATION: Xaa is glutamic acid or cysteine

<400> SEQUENCE: 8

Met Gln Lys Ile Gly Ile Leu Gly Ala Met Arg Xaa Glu Ile Thr Pro
1               5                   10                  15

Ile Leu Glu Leu Phe Gly Val Asp Phe Glu Glu Ile Pro Leu Gly Gly
            20                  25                  30

Asn Val Phe His Lys Gly Val Tyr His Asn Lys Glu Ile Ile Val Ala
        35                  40                  45

Tyr Ser Lys Xaa Gly Lys Val His Ser Thr Leu Thr Thr Thr Ser Met
    50                  55                  60

Ile Leu Ala Phe Gly Val Gln Lys Val Leu Phe Ser Gly Val Ala Gly
65                  70                  75                  80

Ser Leu Val Lys Asp Leu Lys Ile Asn Asp Leu Leu Val Ala Thr Gln
                85                  90                  95

Leu Val Gln His Asp Val Asp Xaa Ser Ala Phe Asp His Pro Leu Gly
            100                 105                 110

Phe Ile Pro Glu Ser Ala Ile Phe Ile Glu Thr Ser Gly Ser Leu Asn
        115                 120                 125
```

-continued

```
Ala Leu Ala Lys Lys Ile Ala Asn Glu Gln His Ile Ala Leu Lys Glu
    130                 135                 140

Gly Val Ile Ala Ser Gly Asp Gln Xaa Val His Ser Lys Glu Arg Lys
145                 150                 155                 160

Glu Phe Leu Val Ser Glu Phe Lys Ala Ser Ala Val Glu Xaa Glu Gly
                165                 170                 175

Ala Ser Val Ala Phe Val Cys Gln Lys Phe Gly Val Pro Cys Cys Val
                180                 185                 190

Leu Arg Ser Ile Ser Asn Asn Ala Asp Glu Lys Ala Gly Met Ser Phe
        195                 200                 205

Asp Glu Phe Leu Xaa Lys Ser Ala His Thr Ser Ala Lys Phe Leu Lys
    210                 215                 220

Ser Met Val Asp Glu Leu
225                 230
```